(12) United States Patent
Serrahima Tornel et al.

(10) Patent No.: US 12,011,180 B2
(45) Date of Patent: Jun. 18, 2024

(54) APPARATUS AND METHODS FOR REPAIRING AN INTERVERTEBRAL DISC

(71) Applicant: Neos Surgery, S.L., Cerdanyola del Valles (ES)

(72) Inventors: Marc Serrahima Tornel, Catalunya (ES); Salvador Llas Vargas, Rellinars (ES); Ana Rodríguez Alonso, Sant Vicenç Dels Horts (ES); Lluís Chico Roca, Badalona (ES)

(73) Assignee: Neos Surgery, S.L., Cerdanyola del Valles (ES)

( * ) Notice: Subject to any disclaimer, the term of this patent is extended or adjusted under 35 U.S.C. 154(b) by 617 days.

(21) Appl. No.: 17/220,106

(22) Filed: Apr. 1, 2021

(65) Prior Publication Data
US 2021/0290254 A1 Sep. 23, 2021

Related U.S. Application Data

(63) Continuation-in-part of application No. PCT/ES2020/070574, filed on Sep. 25, 2020.

(30) Foreign Application Priority Data

Sep. 27, 2019 (ES) .......................... ES201931564 U

(51) Int. Cl.
*A61B 17/16* (2006.01)
*A61B 17/86* (2006.01)
(Continued)

(52) U.S. Cl.
CPC ...... *A61B 17/1604* (2013.01); *A61B 17/1671* (2013.01); *A61B 17/86* (2013.01); *A61B 17/8875* (2013.01); *A61B 2090/3966* (2016.02)

(58) Field of Classification Search
CPC ............ A61B 17/1604; A61B 17/1662; A61B 17/1671; A61B 17/8875
See application file for complete search history.

(56) References Cited

U.S. PATENT DOCUMENTS

2017/0007409 A1* 1/2017 Mauldin ................ A61B 17/88

FOREIGN PATENT DOCUMENTS

WO 2009094493 A2 7/2009
WO WO-2009094493 A2 * 7/2009 ........... A61B 17/025

OTHER PUBLICATIONS

International Search Report and Written Opinion received in international application No. PCT/ES2020/070574, dated Feb. 4, 2021 (12 pages).

* cited by examiner

*Primary Examiner* — Si Ming Ku
(74) *Attorney, Agent, or Firm* — Edell, Shapiro & Finnan, LLC

(57) ABSTRACT

Disclosed are tools and devices for use in repairing an intervertebral disc. The devices include an anchor configured to be secured in a vertebra adjacent the intervertebral disc and a prosthesis having an active part that is configured for placement inside the nucleus of the disc. The tools include an anchor placement tool that includes a chisel for carving the vertebra and a rotatable part that is used for engaging with and screwing the anchor into the vertebra. The tools also include a prosthesis placement tool that is configured to support and facilitate an attachment of the prosthesis to the anchor and to deploy the active part of the prosthesis in the nucleus of the disc. According to one embodiment the prosthesis placement tool is equipped with electronics for the purpose of verifying a corrected attachment of the prosthesis to the anchor. According to other (Continued)

embodiments, the electronics are included in a separate checker tool.

18 Claims, 29 Drawing Sheets

(51) Int. Cl.
*A61B 17/88* (2006.01)
*A61B 90/00* (2016.01)

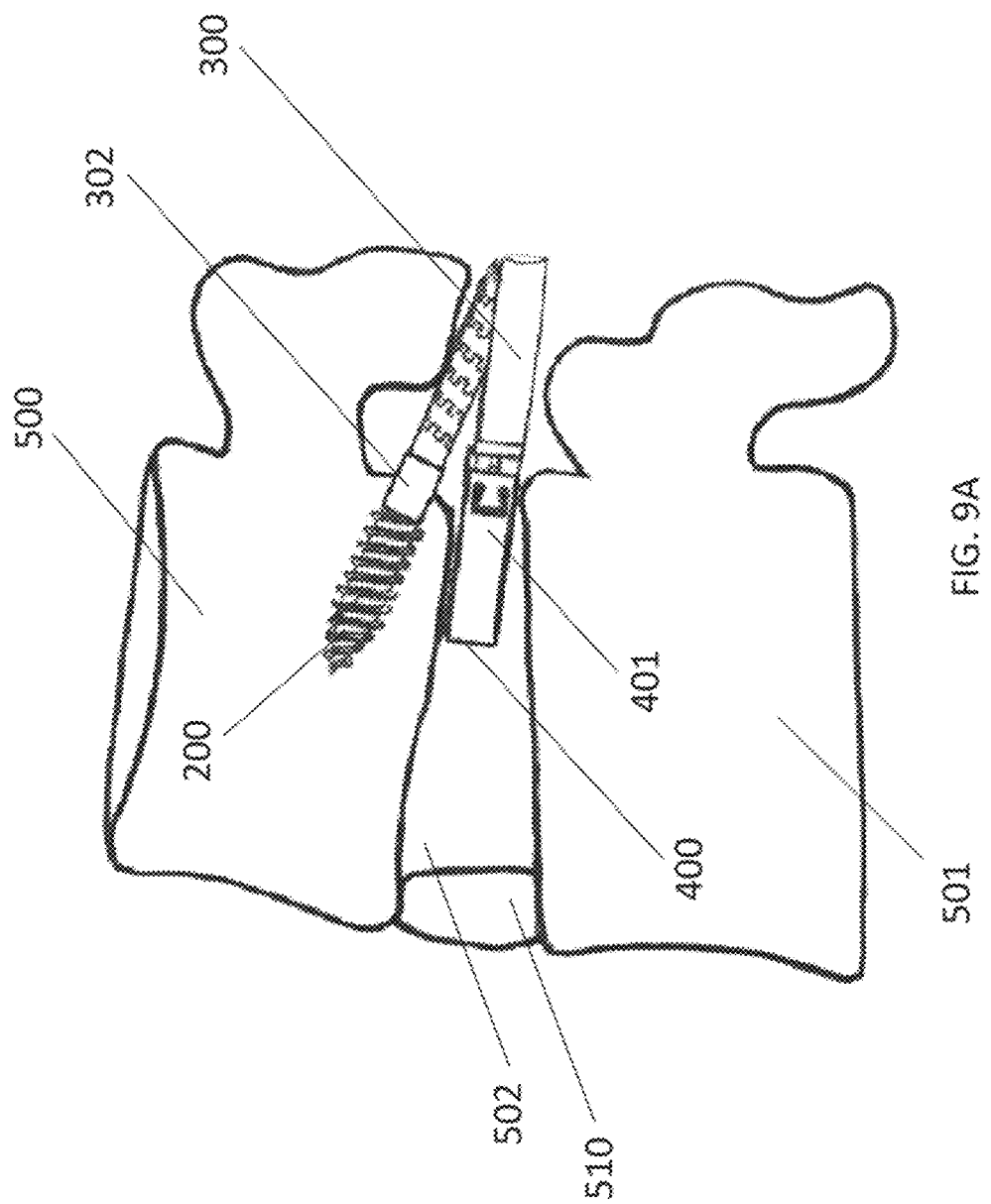

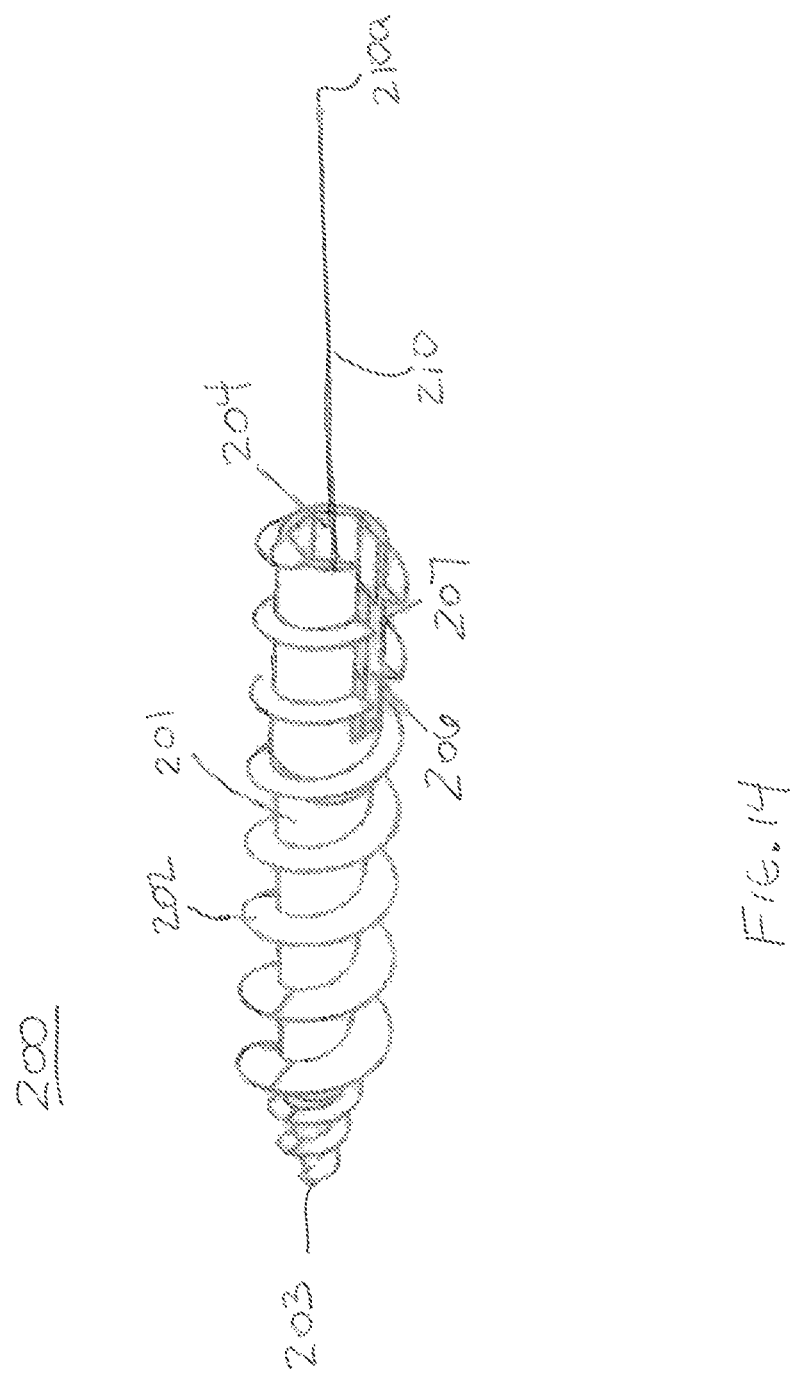

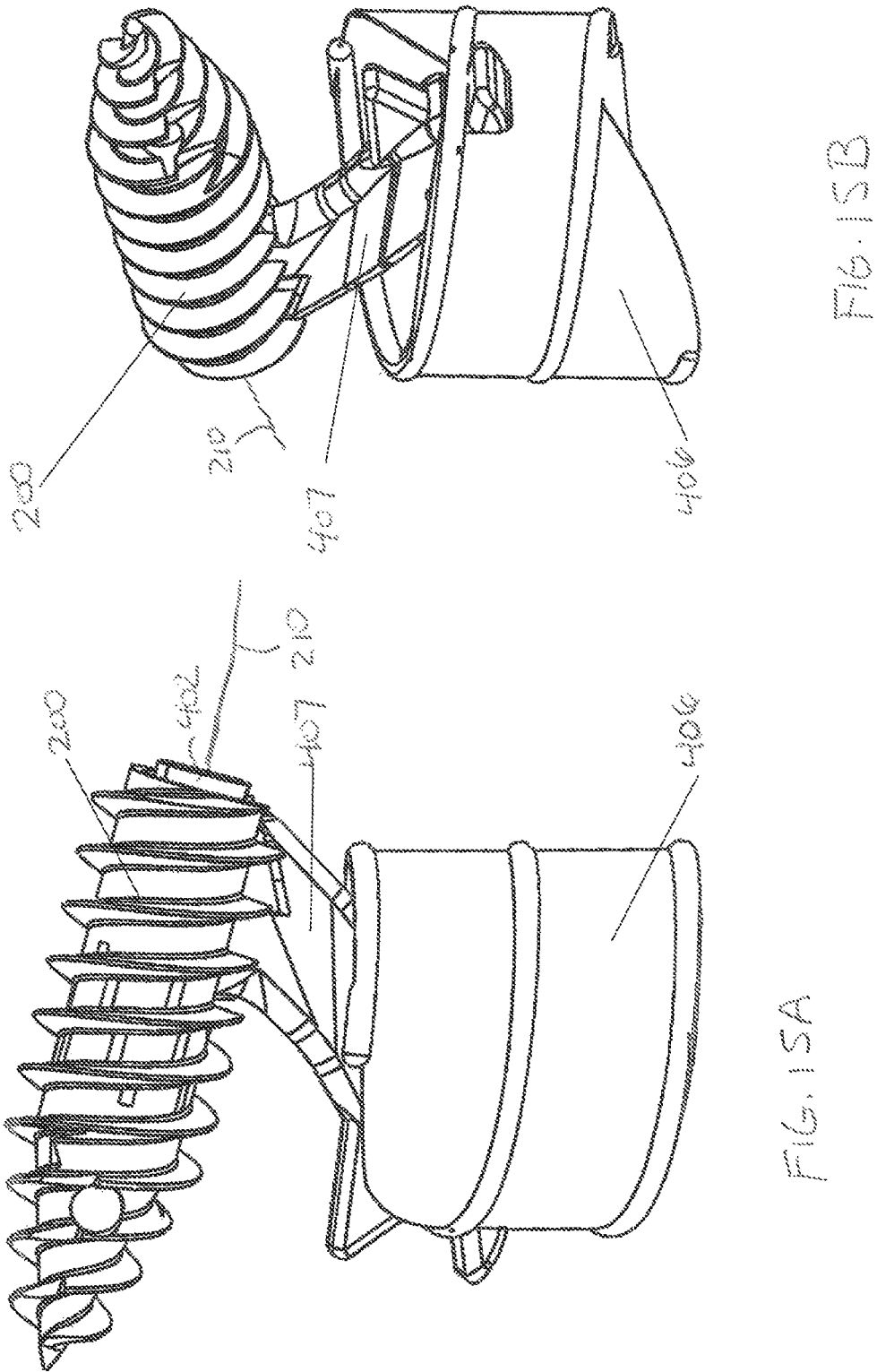

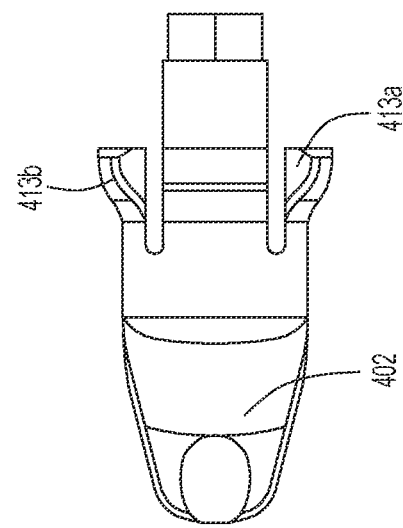
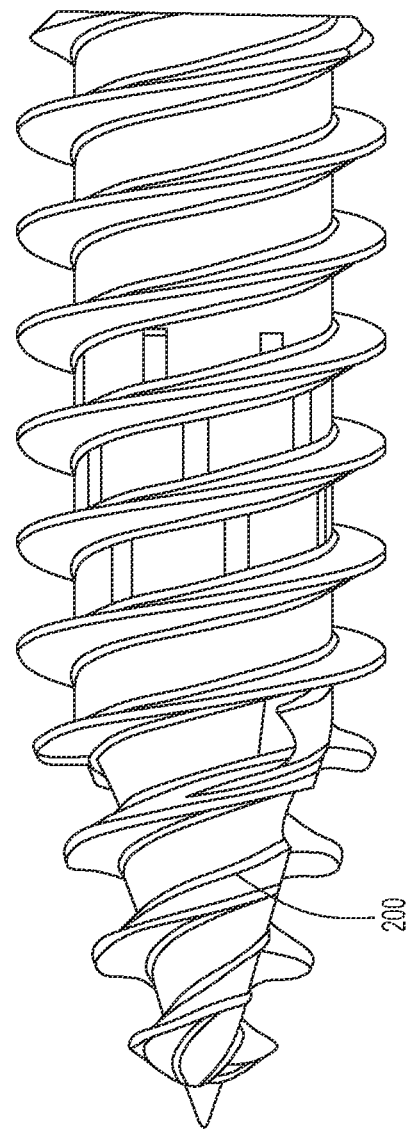
FIG.16

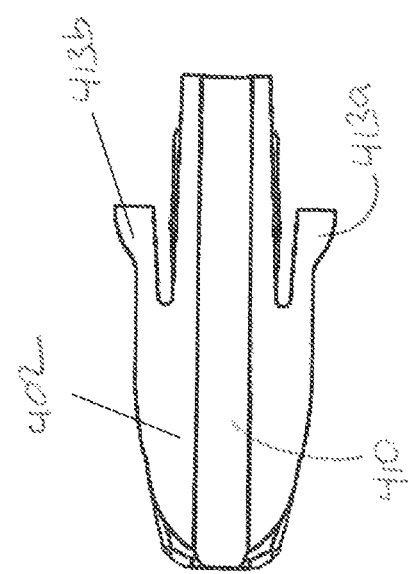
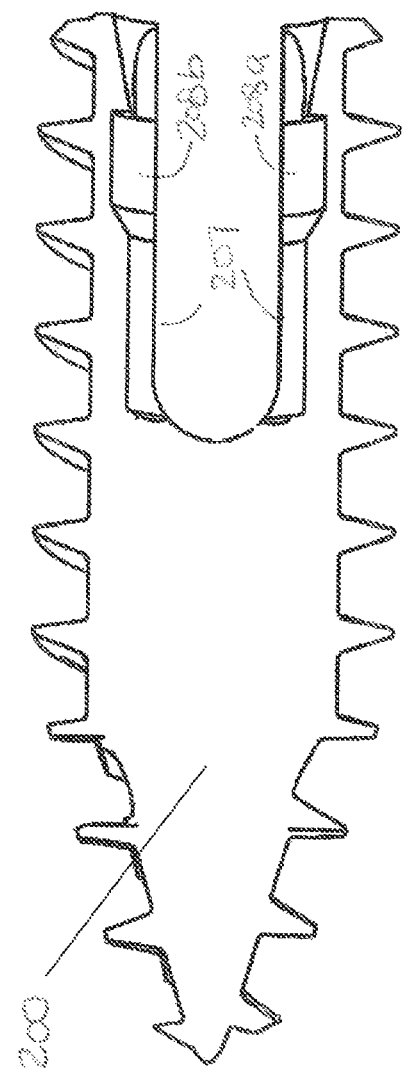
FIG. 17A

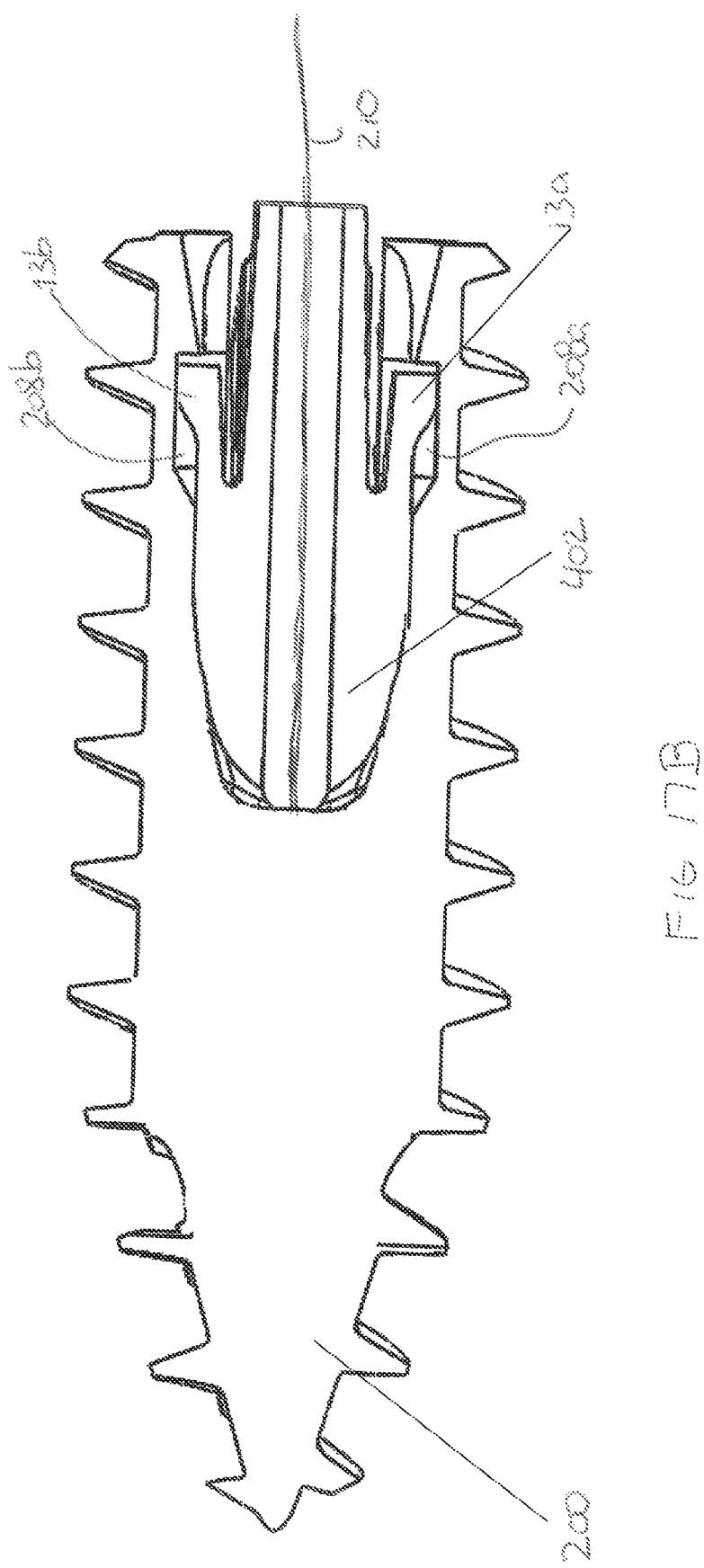

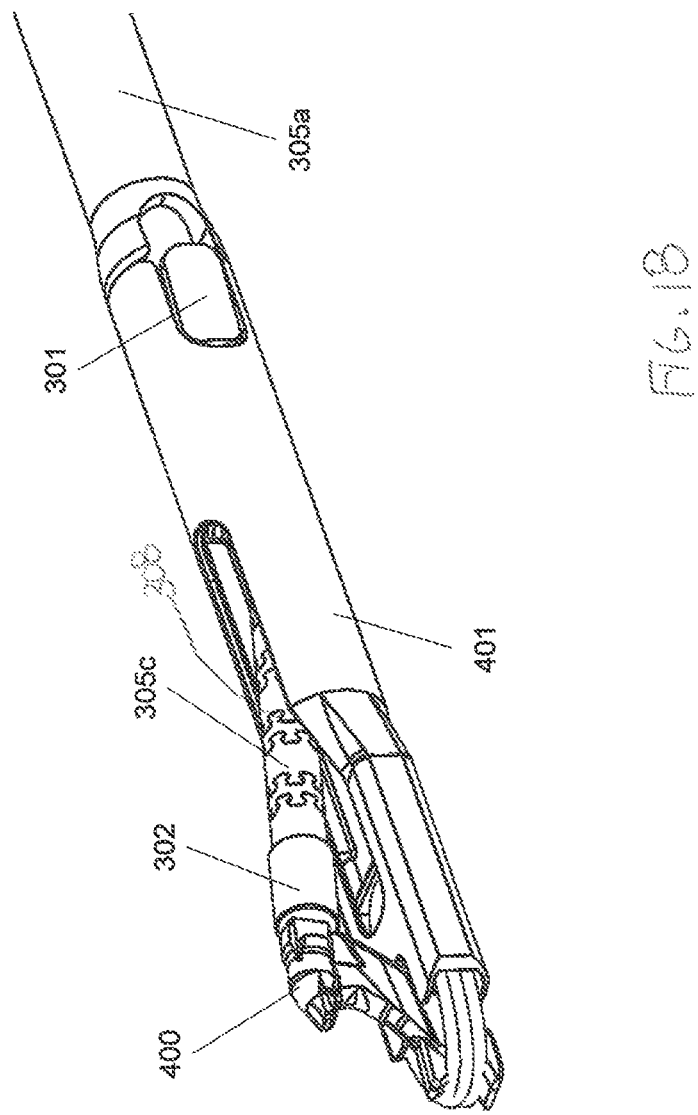

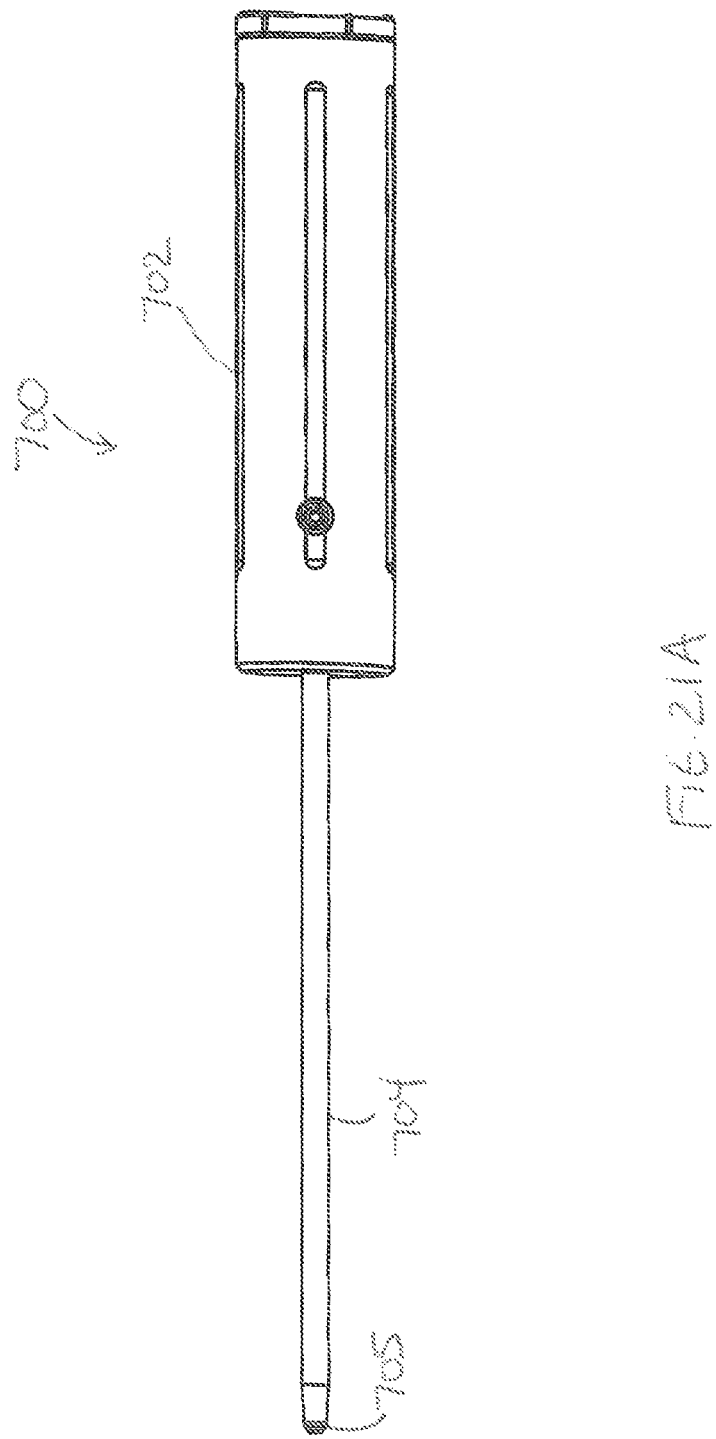

APPARATUS AND METHODS FOR REPAIRING AN INTERVERTEBRAL DISC

CROSS-REFERENCE TO RELATED APPLICATIONS

This application is a continuation-in-part of and claims the benefit and priority to International Application No. PCT/ES2020/070574, filed Sep. 25, 2020, which claims the benefit and priority to Spanish Utility Model Patent Application No. U201931564, filed Sep. 27, 2019.

FIELD

Tools for implanting an anchor and prosthesis for the purpose of repairing an intervertebral disc. The tools including a first tool that includes a chisel, the first tool specially adapted for placing an anchor in a vertebra adjacent an intervertebral disc in order to subsequently be able to couple a prosthesis to the anchor with a second tool, such that the prosthesis is properly positioned in the intervertebral disc.

BACKGROUND

During a surgical intervention to place a vertebral prosthesis, the positioning of the prosthesis to be placed in the intervertebral disc must be carried out with precision, since an incorrect placement could prevent the correct functioning of the prosthesis, it even being necessary to intervene surgically again to reposition or remove the prosthesis.

For the placement of prostheses in the intervertebral disc, solutions are known based on first incorporating an anchor in a vertebra and subsequently coupling a prosthesis to the anchor, thus allowing, if the anchor is properly placed in the vertebra, the prosthesis to be properly placed when coupling the prosthesis to the anchor.

This type of anchor can be placed by the use of a tool having a chisel part that enables the vertebra to be carved to expose the area in which the anchor will be fixed, to subsequently place the anchor in the exposed area carved by means of the chisel, for example, by screwing it with a screwdriver.

However, as these types of anchors are very small, during the surgical intervention it is extremely difficult to be able to ensure that the anchor is properly placed in the vertebra, which can lead to unnecessary wear of the vertebra if several screwing attempts are carried out. Furthermore, it is also very difficult to insert the anchor sufficiently for it to be correctly secured to the vertebra without it being excessively inserted and not enabling the prosthesis to be correctly coupled.

SUMMARY

According to one embodiment, an anchor placement tool is provided that is adapted for placing an anchor in a vertebra. The anchor placement tool includes at one end a chisel comprising a cutting mouth adapted for carving the vertebra with a hammer blow in a carving direction, and a handle, adapted for receiving the hammer blows and transmitting them to the cutting mouth. The handle is provided with a fixed handle portion and a rotatable handle portion with respect to the cutting mouth, the cutting mouth and the fixed handle portion being joined by an arm provided with a conduit with an outlet that determines an outlet direction of the conduit, the rotatable handle portion being provided with a rod with a flexible portion and screwing means at the end thereof adapted for screwing an anchor, the rod being adapted for being inserted into the conduit and for advancing in the conduit by rotating the rotatable handle portion with respect to the cutting mouth to screw and place an anchor in the vertebra previously carved in the outlet direction of the conduit, such that the anchor is properly positioned in the vertebra for subsequently coupling a prosthesis. According to one embodiment the rod is a tube having an open distal end that is configured to receive an elongate wire attached to the anchor and protruding distally therefrom.

According to one embodiment, the cutting mouth comprises a punch and a cutting fin, thus enabling the punch to mark and start perforating a point in the vertebra during the carving operation of the vertebra, from which the cutting fin will carve the vertebra, the vertebra portion cut by the fin further enabling the passage of a joining appendix of the prosthesis.

In one embodiment, the cutting fin comprises a pointed projection that helps aid the initial positioning of the chisel against the vertebra, leaving the point slightly embedded in the vertebra, preventing the chisel from moving before carving.

According to one embodiment the cutting fin comprises a cutting edge between the punch and the pointed projection, enabling a cut to be made from the base of the vertebra to be carved, between the pointed projection and the punch. This cutting edge can have a general C-shape, thus enabling it to enter the vertebra progressively, facilitating the cutting thereof.

According to one embodiment the end of the punch is advanced in the carving direction with respect to the end of the pointed projection, such that when the chisel is applied against the vertebra, the end of the pointed projection is slightly embedded in the vertebra when the punch has already cut a portion of the base of the vertebra and has entered the intervertebral space by piercing the annulus fibrosus arranged between the vertebrae.

According to one embodiment the cutting edge extends radially with respect to the carving direction, in order to thus enable a straight cut in the vertebra to be made that subsequently enables a portion of a prosthesis that is secured in the anchor to be housed. The cutting edge is intended to extend radially with respect to the carving direction in a vertical direction, to thus form a vertical straight cut in the vertebra.

The cutting mouth of the chisel may be provided with guiding means of the carving direction, such that tracking is possible during the carving operation of the vertebra in order to verify that the vertebra is being carved in the correct direction. The guiding means of the carving direction can be a set of perforations aligned in the cutting mouth, such that if the cutting mouth is metal, it will be possible to track the carving direction for example by means of X-ray imaging. Naturally, the same effect will be achieved when the cutting mouth is radio-opaque to the rays from which the tracking image is generated. According to one embodiment the perforations are arranged in a straight line. In instances when the chisel is not made of a radiopaque material, the perforations may be substituted with radiopaque markers.

It is disclosed that the cutting mouth can also be provided with a maximum carving mark, which can also be a perforation in the cutting mouth, such that if the cutting mouth is metal, it will be possible to track the carving depth, for example, by means of X-ray imaging.

According to one embodiment the fixed handle portion of the anchor placement tool is provided with a threaded shaft, and the rotatable handle portion is provided with a thread complementary to the threaded shaft and adapted for enabling the rotatable handle portion to rotate with respect to the fixed handle portion, thus enabling the speed at which the rod advances along the conduit when rotating the rotatable handle portion to be adjusted, appropriately sizing the passage of this threaded shaft and thread. According to one embodiment, the thread passage of the handle is compatible with the thread passage of the anchor, such that the rotation and advancement of the rod can be correctly transmitted to the anchor during screwing of the anchor to the vertebra, for example, the thread passage of the anchor and that of the handle being equal. Alternatively, if the fixed handle portion is devoid of a threaded shaft, and the rotatable handle portion is devoid of a complementary thread, the advancement of the rod along the conduit will be conditioned by the thread passage of the anchor, when screwed to a vertebra.

The handle is preferably provided with path limiting means of the rotation of the rotatable handle portion with respect to the fixed handle portion, to thus limit the advancement of the rod through the conduit and limit the screwing depth of the anchor in the vertebra and furthermore, to be able to determine the final angular position of the screwing means and, consequently, of the anchor screwed to the vertebra. Being able to determine the final angular position of the anchor screwed into the vertebra is important in order to thus ensure that a prosthesis that is subsequently coupled to the anchor is properly positioned. Preferably, when the fixed handle portion is provided with a threaded shaft, and the rotatable handle portion is provided with a thread complementary to the threaded shaft and adapted for enabling the rotatable handle portion to rotate with respect to the fixed handle portion, the path limiting means can be a path end or a stop formed in the complementary thread or the threaded shaft, which will limit the rotation of the rotatable handle portion with respect to the fixed handle portion, said path limiting means being able to be incorporated during the manufacture of the threaded shaft or complementary thread.

In one embodiment, the conduit comprises an angled section between the carving direction and the outlet direction, carrying out a smooth transition between the carving direction and the outlet direction of the conduit.

In one embodiment, the cutting mouth comprises support means that enables the cutting mouth to be supported on a lower vertebra while the upper vertebra is being carved, thus enabling the stability of the chisel to be improved and making it easier to follow a correct carving direction, as well as enabling the operation of screwing and anchor placing to be carried out without the chisel moving.

According to one embodiment the support means comprises fins, such as two fins, which extend in opposite directions in a direction perpendicular to the carving direction, thus determining a suitable lower support surface for supporting the chisel on the vertebra immediately below the intervertebral disc during the carving operation.

Also provided is a prosthesis placement tool adapted for coupling a prosthesis to the anchor previously placed in the upper vertebra by means of the anchor placement tool.

According to some embodiments, a kit is provided that includes the anchor placement tool and the prosthesis placement tool. The kit may further comprise an anchor adapted for being applied to the vertebra by the anchor placement tool and a prosthesis adapted for being coupled to the anchor by means of the prosthesis placement tool. An active part of the prosthesis may be housed in a sleeve with the sleeve being attached to a distal end portion of a first tube that extends distally from a rotatable grip. The prosthesis placement tool also includes push means adapted for pushing the prosthesis out of the sleeve to couple it to the anchor.

According to one embodiment, the rotatable grip is operatively connected to the push means situated at a distal end of a second tube that extends distally from the grip, the assembly adapted for carrying out a linear movement of the push means when the grip is rotated. The rotatable grip is also operatively connected with the first tube to which the sleeve is connected, spindle assemblies located inside the grip being adapted for carrying out a linear movement of the first tube in a direction opposite to a linear movement of the second tube when the grip is rotated. That is, an end of the second tube is moved in a distal direction away from the grip and the end of the first tube moves in a proximal direction towards the grip. According to one embodiment the first and second tubes are concentric and the spindle assemblies comprise respective concentric spindle nut assemblies.

According to one embodiment the first and second tubes of the prosthesis placement tool are removably coupled to the spindle nut assemblies, such that they can be separated from the spindle nut assemblies to be disinfected after each use.

According to some embodiments the prosthesis includes a connector part that is configured for placement inside an opening of the anchor for the purpose of securing the prosthesis to the anchor. Also disclosed herein are checking means configured to determine if the connector part of the prosthesis has been fully and properly introduced into the opening of the anchor. According to one embodiment the checking means is integrated with the prosthesis placement tool, while in other embodiments comprises a stand-alone checker tool separate from the prosthesis placement tool. Each of these devices includes a battery-powered electric circuit having an acoustic device (e.g. an electronic bell) electrically coupled to a first pole of the battery. Each of these embodiments also comprises a handle and an electrically conductive elongate tube that extends distally from the handle, a distal end of the elongate tube being configured to contact the body of the anchor (which is also electrically conductive) when the connector part is properly secured to the anchor. According to one embodiment, the elongate tube is electrically coupled to the first pole of the battery. Each of the checker tools are configured to receive in them a proximal end portion of an electrically conducive elongate wire whose distal end is coupled to the anchor. In use, the elongate wire passes through the elongate tube until it is directly or indirectly electrically coupled to the second pole of the battery. As a result of this configuration, when a distal end of the elongate tube successfully makes physical contact with the anchor while the elongate wire is electrically coupled to the battery, a closed electrical circuit is established. This allows current to flow through the circuit to thereby cause an activation of the acoustic device so that it produces a sound. The anchor, the connector part of the prosthesis and the distal end of the elongate tube are configured such that the distal end of the elongate tube can only make contact with the anchor upon the connector being properly and fully inserted inside the housing of the anchor.

These and other advantages and features will become evident in view of the drawings and detailed description.

BRIEF DESCRIPTION OF THE DRAWINGS

As a complement to the present disclosure, and for the purpose of helping to make the features more readily understandable, the description is accompanied by a set of drawings which, by way of illustration and not limitation, represent the following:

FIGS. 9A and 9B show a placing sequence of a prosthesis by means of the prosthesis placement tool of FIG. 6;

FIG. 14 illustrates a perspective side view of an anchor according to one embodiment;

FIGS. 15A-C illustrate various perspective views of a prosthesis attached to an anchor;

FIG. 16 is a side view of a connector of the prosthesis ready for placement inside a housing of the anchor;

FIG. 17A is a cross-section side view of the assembly of FIG. 16.

FIG. 17B is a cross-section side view of the assembly of FIG. 16 with the connector inserted and locked inside the housing of the anchor;

FIG. 18 is a perspective view of an end portion of an anchor placement tool according to another embodiment;

FIG. 21A is a side view of a checker tool that is configured to determine a proper placement of the prosthesis connector inside the housing of the anchor;

DETAILED DESCRIPTION

In the disclosure that follows, the terms "proximal", "distal" and variations thereof are used to denote relative placement and movement. In most instances the context of the disclosure readily reveals the distinction between "proximal" and "distal". In general, the terms "proximal" and "distal" are used herein to denote a location with respect to the intended location of the surgeon/clinician using the devices, the term "proximal" denoting a location nearer or in a direction of the surgeon/clinician and the term "distal" denoting a location away from or in a direction away from the surgeon/clinician.

Figure 1:
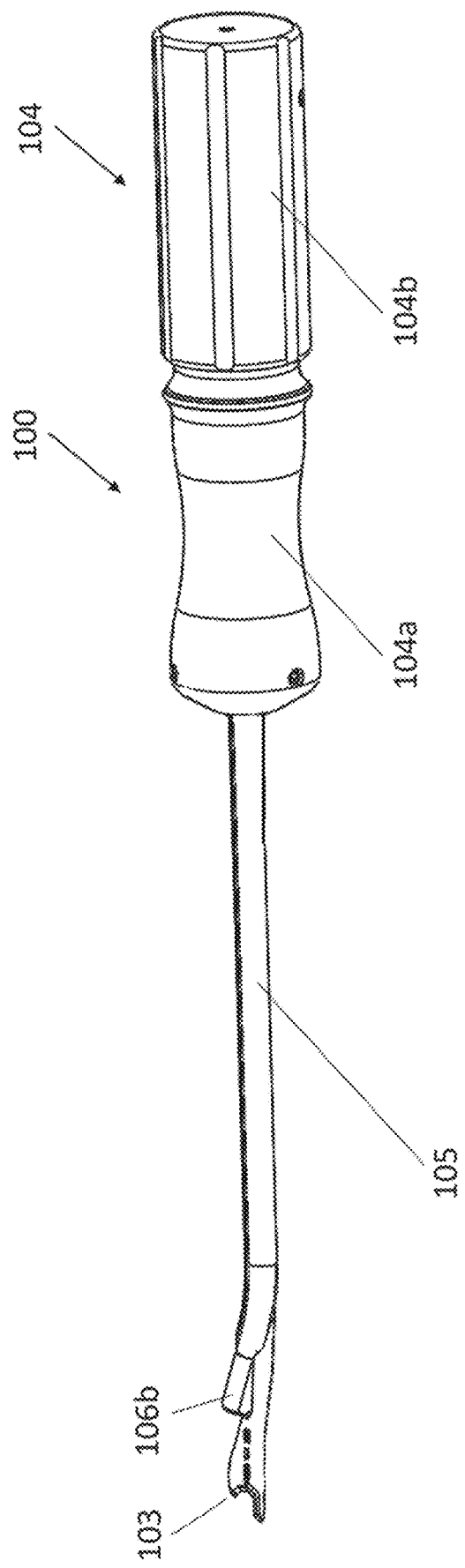
FIG. 1 illustrates a side view of an anchor placement tool according to one embodiment.

The anchor placement tool 100 of FIG. 1 is specially adapted for placing an anchor 200 in a vertebra adjacent an intervertebral disc. As can be seen, the anchor placement tool 100 comprises a chisel in the form of cutting mouth 103 adapted for carving a vertebra with a hammer blow in a carving direction d1, and a handle 104, adapted for being struck by a hammer or the like, which is provided with a fixed handle portion 104a and a rotatable handle portion 104b with respect to the cutting mouth 103, the cutting mouth 103 and fixed handle portion 104a being joined by an arm 105. It should be noted that the carving direction d1 corresponds to the longitudinal direction of the tool 100, such that the force exerted when striking the handle 104 is transmitted through the arm 105 to the cutting mouth 103, which will carve or cut a vertebra in that direction. The cutting mouth 103 is thus defined as the sharp part with which a chisel cuts, arranged at one end of the anchor placement tool.

Figure 2:
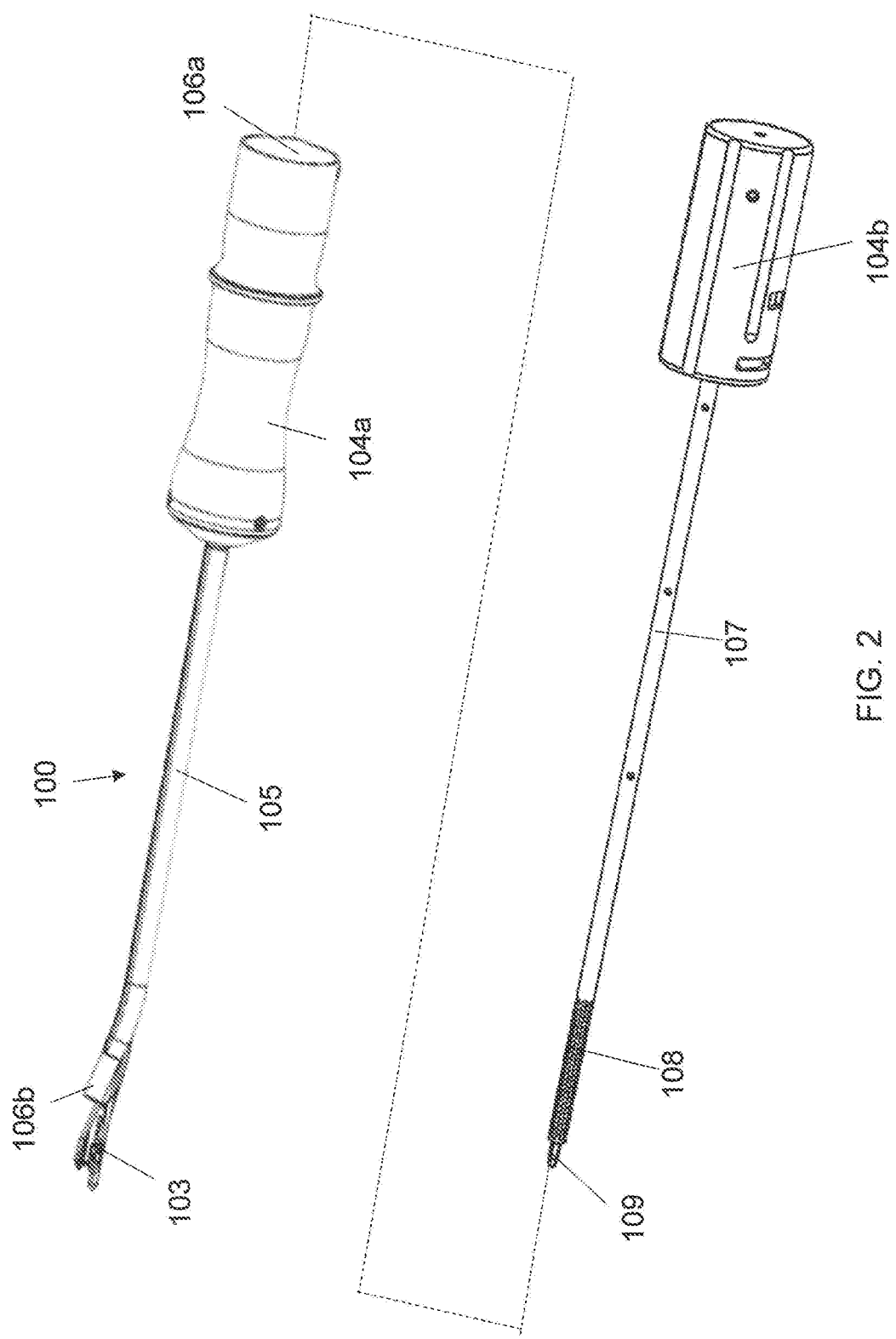
FIG. 2 illustrates the anchor placement tool of FIG. 1 in a disassembled state.
Figure 3:
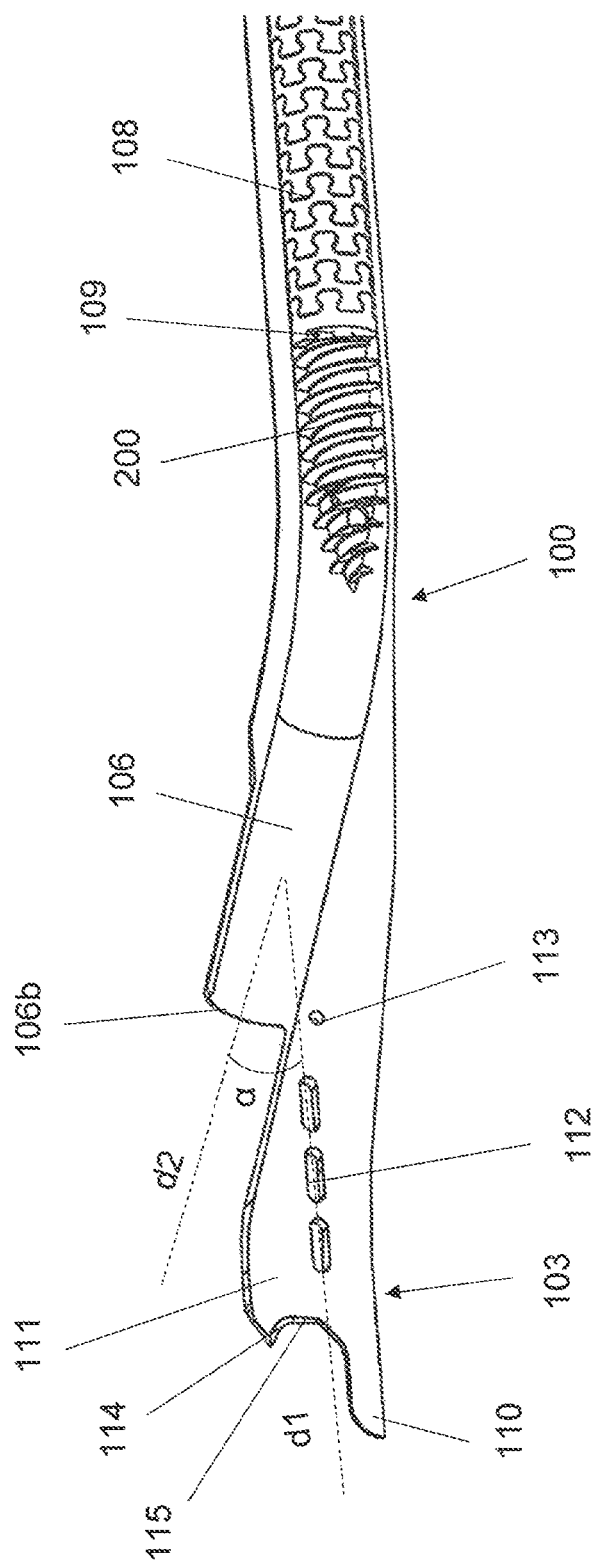
FIG. 3 shows a cross-section of a distal end portion of the anchor placement tool of FIG. 1 with an anchor supported on an end of a rod inside an arm of the anchor placement tool.

As can also be seen in FIGS. 2 and 3, the arm 105 that joins the cutting mouth 103 and the fixed handle portion 104a is advantageously provided with a conduit 106 with an outlet 106b in the arm 105 which determines an outlet direction d2 of the conduit 106 and an inlet 106a in the fixed handle portion 104a, the rotatable handle portion 104b being provided with a rod 107 with a flexible portion 108 and screwing means 109 at the end thereof, such as a screwdriver bit, adapted for securing and screwing an anchor 200, the rod 107 being adapted for being inserted into the conduit 106 and for advancing in the conduit 106 by rotating the rotatable handle portion 104b with respect to the cutting mouth 103 to screw and place an anchor 200 in the vertebra previously inserted in the conduit 106, by way of the screwdriver bit. A distal end portion of the conduit 106 includes an angled/bent/curved section so that the distal outlet mouth 106b of the conduit is arranged facing an outlet direction d2.

As shown in FIG. 3, according to one embodiment the cutting mouth 103 comprises a punch 110 and a cutting fin 111 arranged on the punch, such that the punch 110 enables an initiation of the carving of the vertebra and thus being able to correctly direct the chisel before the cutting fin 111 carves the vertebra to a greater extent, for example by opening a passageway to subsequently house a prosthesis appendage or arm in the anchor 200. The cutting fin 111 of the chisel may also comprise a pointed projection 114 to favor the securing of the cutting fin 111 during the carving operation. For this securing to be achieved, the end of the punch 110 is advanced in the carving direction d1 with respect to the end of the pointed projection 114, such that when the pointed projection 114 is applied against the vertebra, the punch 110 has already entered the intervertebral space and carved the base of the vertebra. To carry out the carving operation, it is observed that the cutting fin 111 comprises a cutting edge 115 in a general C-shape that extends radially with respect to the carving direction d1, in order to thus enable a vertical straight cut to be formed in the vertebra between the punch 110 and the pointed projection 114.

Figure 4A:
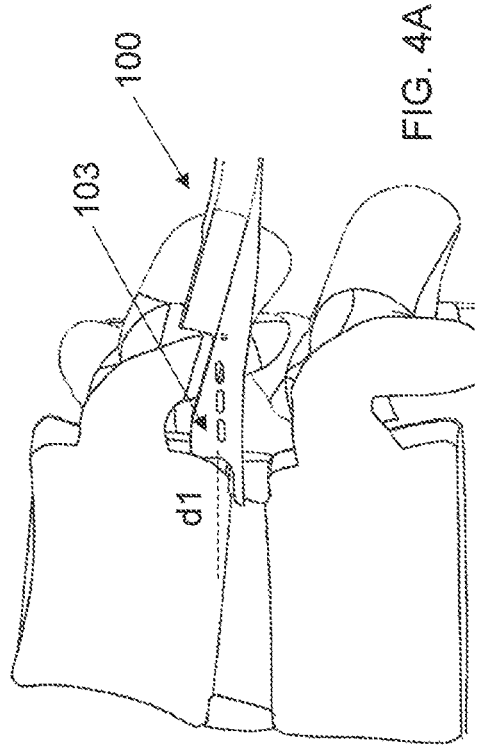
FIGS. 4A through 4C show a sequence of implanting an anchor in a vertebra by means of anchor placement tool of FIG. 1.
Figure 4B:
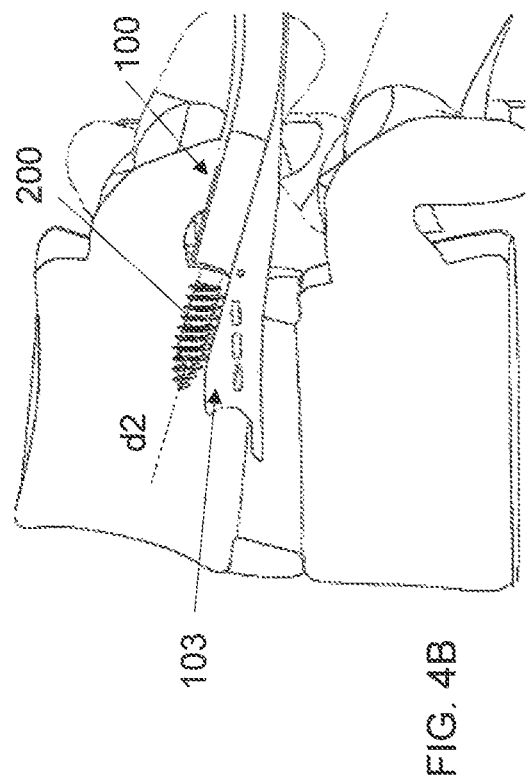
Figure 4C:
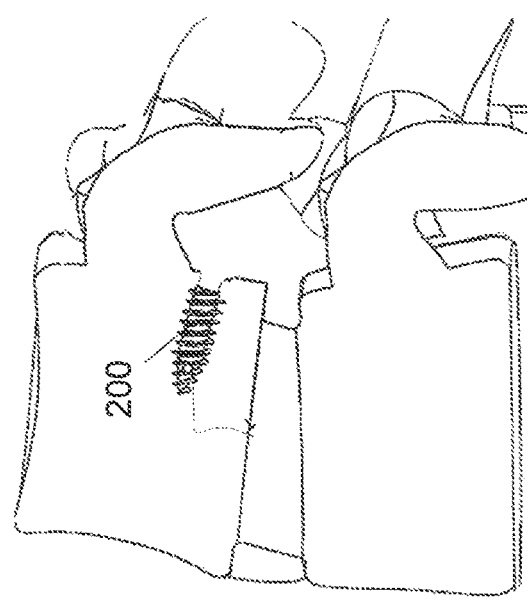

FIGS. 4A to 4C exhibit an example placement sequence of an anchor 200 in a vertebra by means of the anchor placement tool 100, usually on the part of a surgeon during a prosthesis placement operation. Previously, an anchor 200 will have been placed inside the conduit 106 of arm 105 in the conduit 106 (preferably of circular cross section) and secured to the end of the rod 107 by means of the screwing means 109. As noted above, the screwing means may include a screwdriver-like tip, or may include any other form that enables the end of the rod to engage with the anchor so that the anchor is supported on the end of the rod, the screwing means and anchor being configured such that when the rod 107 rotates, so does the anchor.

With continued reference to FIGS. 4A and 4B, the cutting mouth 103 of the chisel is first placed against the vertebra onto which an anchor is to be screwed, as illustrated in FIG. 4A. After sufficiently carving the vertebra in the carving direction d1, as illustrated in FIG. 4A, the outlet direction d2 of the conduit 106 advantageously enables the anchor 200 previously arranged in the conduit 106 and secured by means of the screwing means 109 of the rod 107 to be screwed in the outlet direction d2 as will be seen later in order to ensure the angle α with respect to the carving direction d1 in which the anchor 200 is fixed to a vertebra. This angle α will be an angle that is preferably acute in order to make it easier for the anchor to enter the vertebra, and more preferably less than 45 degrees in order to favor that the anchor is arranged essentially perpendicular to the spinal column. This angle α is predetermined during the manufacture of the anchor placement tool 100, conveniently sizing and positioning the parts thereof.

In order to maintain the carving direction d1 and ensure that the chisel is correctly inserted into the vertebra, the cutting mouth 103 comprises guiding means 112 of the carving direction d1, in this case a set of through holes aligned with respect to the carving direction d1 and which make it possible to track the carving of the chisel 100 by means of X-ray tracking or the like, such that the cutting mouth 103 being metal, the through holes are visible and the carving direction d1 can be tracked, enabling the surgeon to correct the carving direction d1.

Furthermore, it is intended that the cutting mouth 103 of the chisel comprises a maximum carving mark 113, also by way of a through hole, such that the surgeon can determine that the chisel has already entered the vertebra sufficiently and that it is properly positioned to screw and place an anchor 200 previously placed in the conduit 106 in the vertebra.

At this time, when the chisel is properly positioned, the surgeon must rotate the rotatable handle portion 104b, such that the screwing means 109 of the rod 107 advances rotating together with an anchor 200 supported on the screwing means 109 until exiting through the outlet 106b of the conduit 106, duly positioned and forming the predetermined angle α, such that, as the rotatable handle portion 104b continues to rotate, the anchor 200 is screwed and inserted into the vertebra until it is sufficiently secured and placed in the vertebra, as illustrated in FIG. 4B, such that upon removal of the anchor placement tool 100, the anchor 200 is ready to subsequently receive a prosthesis, as shown in FIG. 4C. Furthermore, it should be noted that the cutting mouth 103 will have advantageously left a vertical straight cut in the vertebra suitable for subsequently housing an arm or appendix of the prosthesis. Depending on the type of prosthesis to be included in the anchor 200, the latter must be positioned at a greater or lesser angle with respect to the carving direction d1 and must be inserted to a greater or lesser extent, also depending on the dimensions thereof, which may vary, for example, depending on whether they must withstand a greater or lesser force.

The fixed handle portion 104a may be provided, for example, with a threaded shaft, and the rotatable handle portion may be provided with a thread complementary to the threaded shaft and adapted for joining and enabling the rotatable handle portion 104b to rotate with respect to the fixed handle portion. In this case, by means of sizing the passage of this threaded shaft and thread, it is possible to adjust the speed at which the rod 107 advances along the conduit. It is also intended to be able to size the threaded shaft and thread, as well as the handle 104, such that only a movement of the rod 107 equal to the length that it is desired for the anchor 200 to be inserted into the vertebra is enabled. In this way, the fixed handle portion 104a and the rotatable handle portion 104b can be sized to act as a stop when the rotatable handle portion 104b has been sufficiently rotated. It is also observed that the rod 107 will preferably be hollow and will be provided with perforations that enable the interior thereof to be cleaned and disinfected after use thereof.

The handle 104 of the anchor placement tool 100 may also be provided with path limiting means of the rotation of the rotatable handle portion 104b with respect to the fixed handle portion 104a, for example, path limiting means of the rotation that not only enable the desired length for the anchor 200 to be inserted into the vertebra to be limited but also the final angular position thereof. These path limiting means of the rotation can be, for example, a path end or stop formed in the complementary thread or the threaded shaft. The final angular position in which the anchor 200 will be arranged in the vertebra can be important if it has components on the surface thereof, for example, a lateral channel into which an appendix or arm of the prosthesis must be subsequently inserted, which must be properly positioned.

Figure 5:
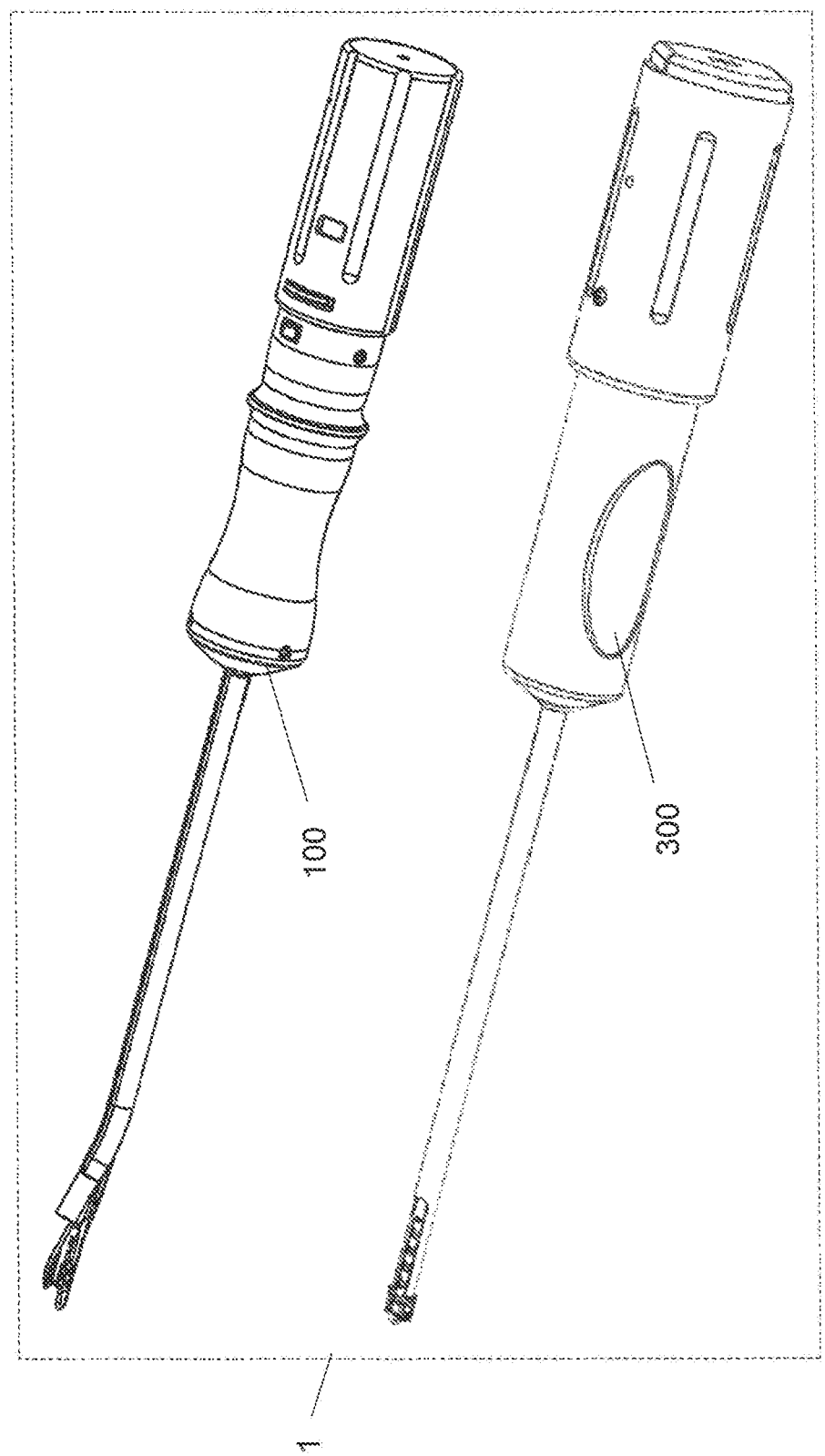
FIG. 5 shows a kit that includes an anchor placement tool and a prosthesis placement tool.

FIG. 5 exhibits a kit 1 for applying a prosthesis in a vertebra by means of an anchor 200. According to one embodiment the kit 1 includes an anchor placement tool 100 adapted for placing the anchor 200 in a vertebra as previously described, and a prosthesis placement tool 300 adapted for coupling a prosthesis 400 to the anchor 200 previously placed in the vertebra. The kit 1 may further comprise the anchor 200 and the prosthesis 400. The anchor placement tool 100, the anchor 200, the prosthesis placement tool 300 and the prosthesis 400 can further be manufactured, marketed or exhibited separately and independently.

Figure 7:
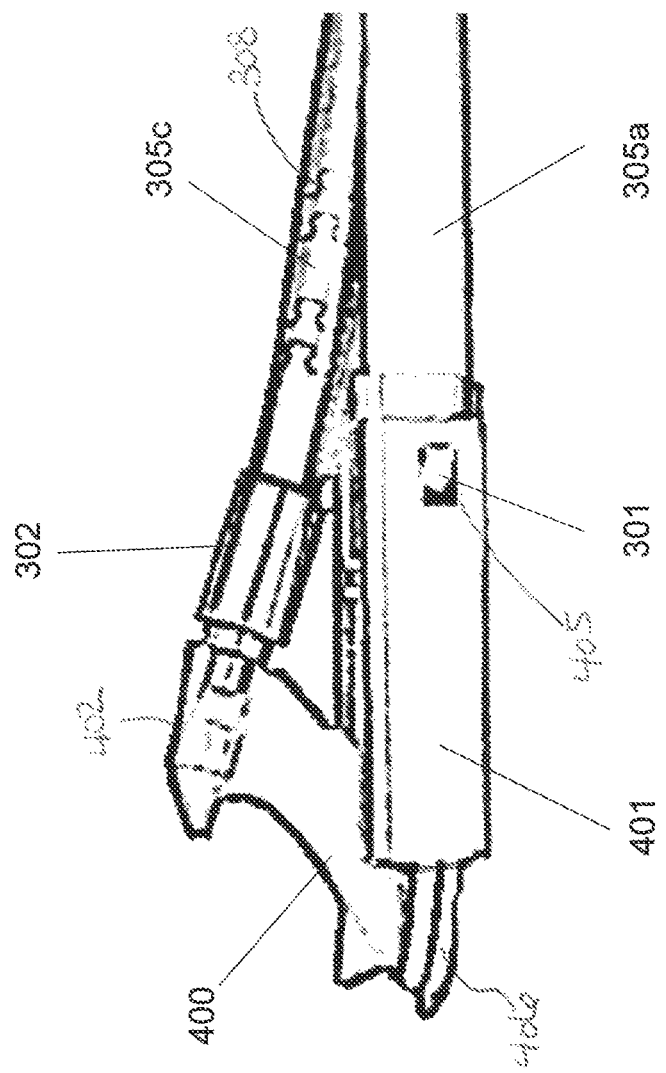
FIG. 7 illustrates an end of the prosthesis placement tool of FIG. 6 with a prosthesis being coupled thereto.
Figure 8:
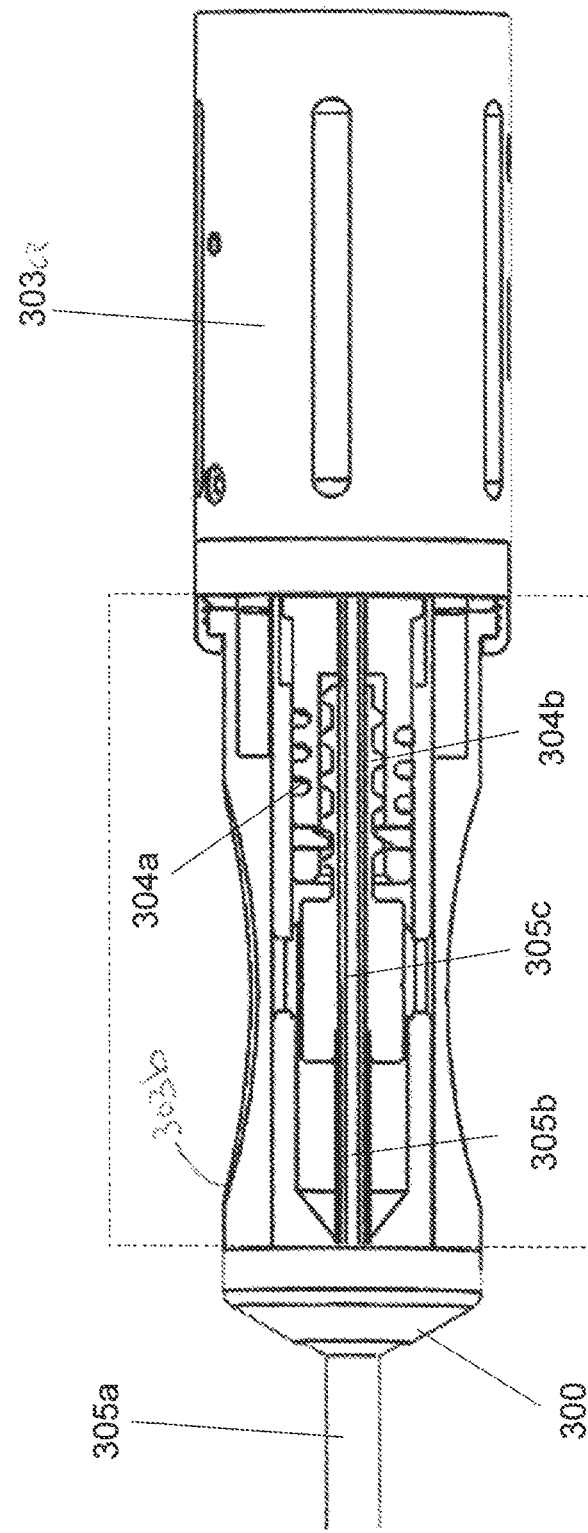
FIG. 8 shows a cross-section view of a portion of the handle of the prosthesis placement tool of FIG. 6.
Figure 15C:
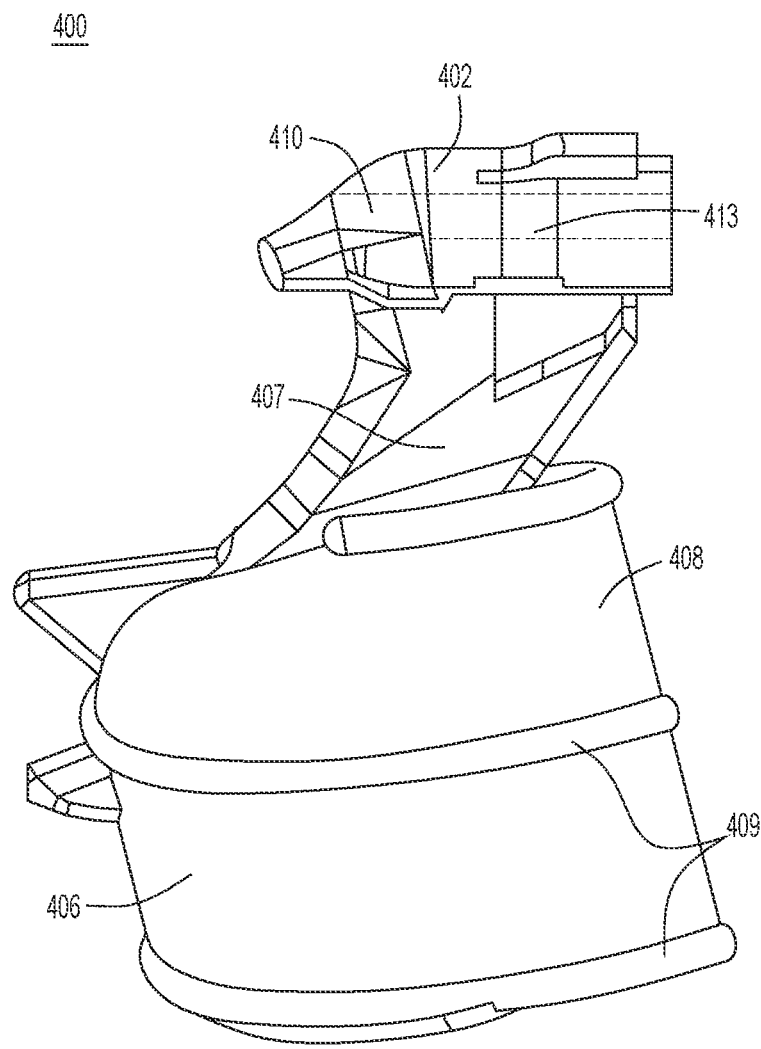

FIG. 14 illustrates a side view of an anchor 200 according to one embodiment. The anchor 200 includes a body 201 having external threads 202 that extend along a substantial length thereof. The anchor includes a distal tip 203 and an internal housing having a proximal open mouth 204. The proximal end portion of the anchor is configured to accommodate a coupling of a connector part of a prosthesis thereto and includes an open groove 206 through which an arm/extension of the prosthesis passes when the prosthesis is coupled to the anchor. As shown in FIGS. 15A-C, according to one embodiment the prosthesis 400 comprises a connector part 402 that is configured to be housed and secured inside the housing of the anchor 200. The prosthesis 400 includes an active part 406 that is connected to the connector part 402 by an arm 407. The active part 406 is suitable for assuming an active expanded shape (as shown in FIGS. 15A-C) suitable for effectuating a closure of a damaged portion of an annulus wall/ring of a intervertebral disc upon the prosthesis 400 having been properly implanted within the nucleus of the disc. According to some embodiments the active part 406 comprises a frame made of one or more filaments 409 arranged to form a plurality of rings that carry with them a membrane 408. The active part 406 is delivered into the nucleus of the disc in a constrained state as shown in FIGS. 7 and 18 and is deployable inside the nucleus of the disc to assume an expanded state as shown in FIGS. 15A-C. The active part 406 may comprise any of a number of other configurations and is not limited to the constructions disclosed herein.

As shown in FIGS. 15A and 15B, when the prosthesis 400 is coupled to the anchor 200, a portion of the arm of the prosthesis extends through the open side channel 206 of the anchor 200.

As generically shown in FIG. 15C, in one embodiment the connector part 402 of the prosthesis 400 includes a leaf spring assembly 413 suitable for being introduced into and locked inside the housing of the anchor 200.

FIGS. 16, 17A and 17B show an example connection arrangement wherein the leaf spring assembly 413 of the connector part 402 of the prosthesis includes first and second leaf springs 413a and 413b located on diametrically opposite sides of the connector part. In their relaxed state, as shown in FIGS. 16 and 17A, leaf springs 413a and 413b radially protrude sufficiently to require that they be deflected radially inward in order for the connector part 402 to pass through the mouth 204 of the anchor 200. The anchor 200 further includes first and second recesses 208a and 208b formed in diametrically opposite internal side walls 207 of the anchor 200 that are respectively configured to receive the first and second leaf springs 413a and 413b as the connector part 402 is fully received inside the housing of the anchor. When the leaf springs 413a and 413b encounter the recesses 208a and 208b as the connector part 402 advances into the housing, they radially expand to occupy the respective recesses to cause the connector part to be locked inside the housing.

As shown in FIG. 14, according to some embodiments the anchor 200 includes an elongate wire 210 that is coupled to an inside of the anchor and extends distally to a location proximal the mouth 204. That is, a proximal end portion 210a of the wire 210 resides outside the housing of the anchor. The function of the wire 210 is discussed in more detail below. In any event, when the anchor 200 does include the elongate wire 210, the connector part 402 of the prosthesis includes a through passage 410 through which the elongate wire passes as the connector part 402 is being attached to the anchor.

Figure 6:
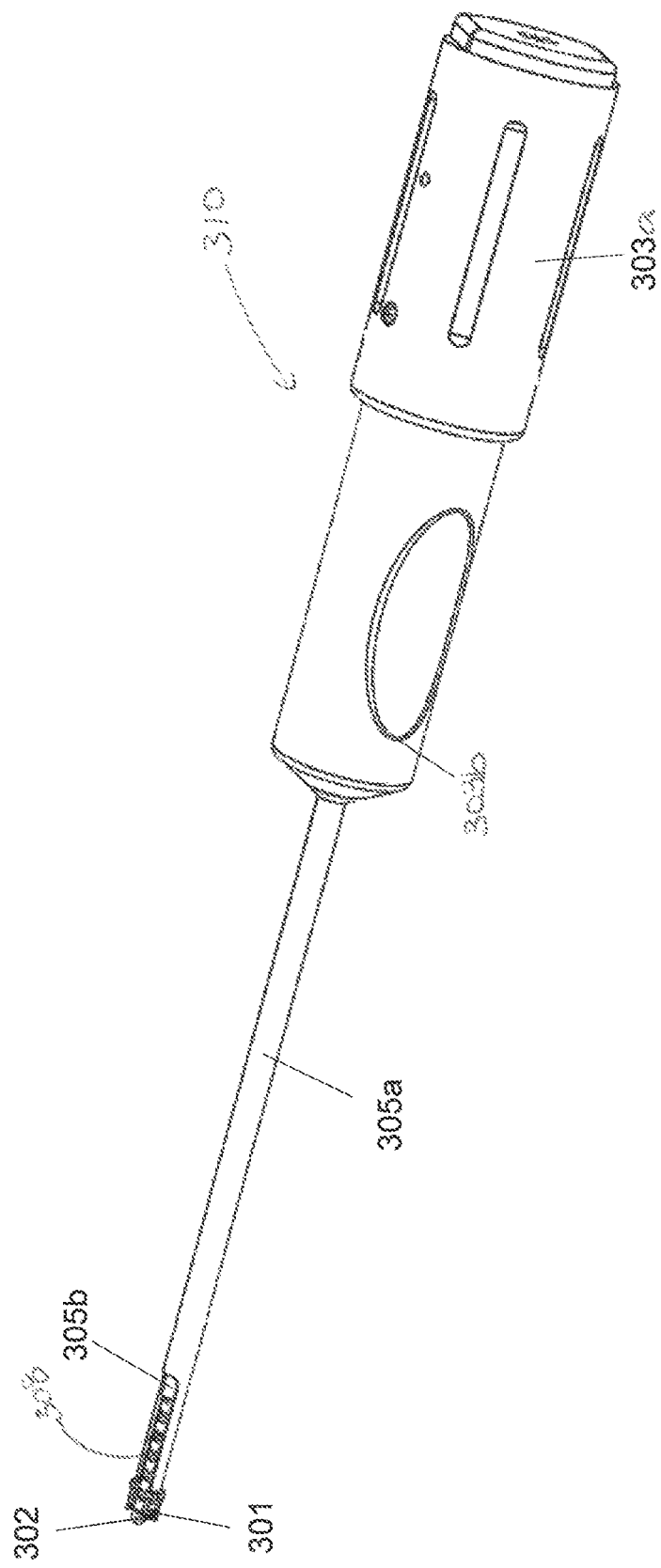
FIG. 6 illustrates a side view of a prosthesis placement tool according to one embodiment.

FIGS. 6 and 7 illustrate a prosthesis placement tool 300 according to one embodiment. As can be observed, the prosthesis placement tool 300 comprises at a distal end thereof securing means 301 that is adapted for securing a sleeve 401 that houses the constrained active part 406 of the prosthesis 400 prior to the active part being implanted inside the nucleus of the disc. The prosthesis placement tool 300 also includes first and second push means 302 and 306. The first push means 302 is configured for pushing the connector part 402 of the prosthesis 400 into the housing of the anchor 200 and the second push means is configured for pushing the active part 406 of the prosthesis 400 out of the sleeve 401 and into the nucleus of the disc.

According to one embodiment, the prosthesis placement tool 300 includes first, second and third tubes 305a, 305b and 305c. In some instances, tube 305c is instead a solid rod. The handle 310 includes a rotatable grip 303a that extends proximally from a fixed handle portion 303b. The rotatable grip 303a is operatively coupled to first and second spindle nut assemblies 304a and 304b that are in turn respectively and operatively coupled to the first and second tubes 305a and 305b. According to one embodiment, at least a portion of the second tube 305b is located inside a conduit of the first tube 305a and at least a portion of the third tube 305c is located inside the second tube 305b. As will be discussed in more detail below, as the rotatable grip 303a is rotated in a first direction the spindle nut assemblies 304a and 304b respectively act to cause a distal end of the first tube 305a to move proximally towards the handle 310 and to cause the push means 306 located at the distal end tube 305b to move distally away from the handle 310. According to one embodiment, the first and second spindle nut assemblies are concentrically aligned. According to one embodiment, the second and third tubes 305b and 305c are respectively separable from the handle 310 to facilitate a disinfecting of the tubes after their use.

As shown in FIG. 7, in use the prosthesis 400 is initially coupled to a distal end portion of the prosthesis placement tool 300. In the embodiment of FIG. 7, the active part 406 of the prosthesis 400 is loaded in a constrained state inside a sleeve 401 that is attached to the end of tube 305a by tabs 301 that extend through openings 405 located on opposite sides of the sleeve. A pusher 302 located at the end of tube 305c is also coupled to a proximal end of the connector part 402 of the prosthesis 400. In the embodiment of FIG. 18, the sleeve 401 includes an elongate proximal portion that is coupled to the end of tube 305a by the use of flaps 301 that can be closed to secure the sleeve to tube 305a and opened to release the sleeve from tube 305a. The use of a longer sleeve advantageously moves the connection location of the sleeve and tube 305a away from the implantation site of the prosthesis so that it doesn't obscure the surgeon's view of the implantation site.

In the embodiment of FIGS. 6 and 7, distal end portions of each of tubes 305a and 305b comprise elongate lateral openings that enable a passage of a flexible end portion 308 of tube 305c to bend outside tubes 305a and 305b to enable the pusher 302 at the end of tube 305c to be coupled to the connector part 402 of the prosthesis as shown in FIG. 7.

Figure 10A:
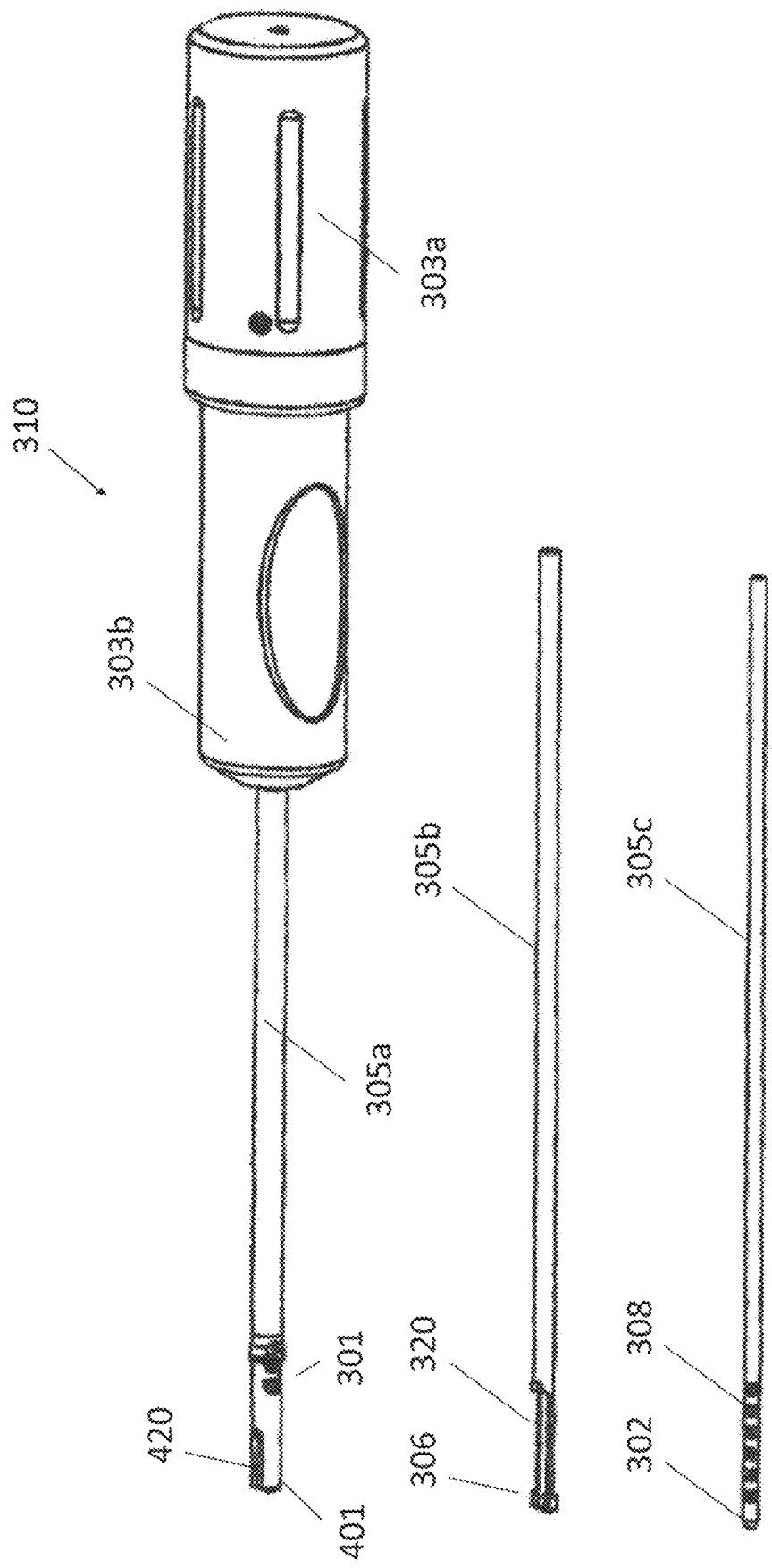
FIG. 10A shows the prosthesis application tool of FIG. 6 in a disassembled state.
Figure 10B:
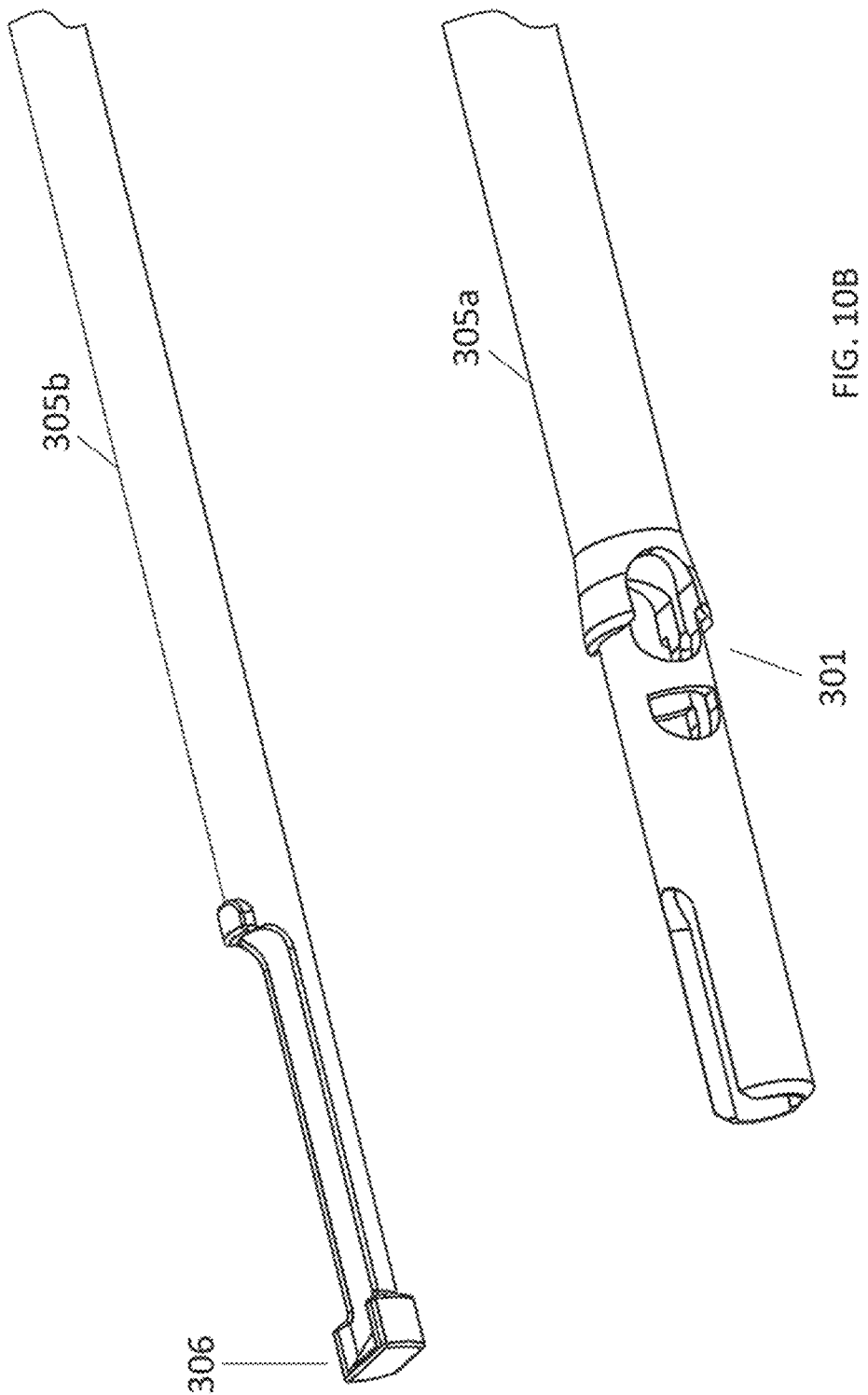
FIG. 10B show an enlarged view of the tubes of the prosthesis placement tool shown in FIG. 10A.

In the embodiment of FIGS. 10A, 10B and 18, the distal end portions of each of the sleeve 401 and tube 305b respectively includes an elongate lateral opening 420 and 320 that enable a passage of the flexible end portion 308 of tube 305c to bend outside sleeve 401 and tube 305b to enable the pusher 302 at the end of tube 305c to be coupled to the connector part 402 of the prosthesis as shown in FIG. 18.

The prosthesis placement tool 300 is configured to facilitate an attachment of the connector part 402 of the prosthesis 400 to the anchor 200 previously secured to the vertebra and to also facilitate a deployment of the active part 406 of the prosthesis into the nucleus of the disc to be repaired. In the method illustrated in FIGS. 9A and 9B, after the prosthesis 400 has been secured to the end of the prosthesis placement tool 300 as described above, the apparatus is distally advanced toward the repair site so that the connector part 402 of the prosthesis 400 is forced into the housing of the anchor 200 by the pusher 302 located at the end of tube 305c and so that at least a portion of the sleeve 401 that houses the active part 406 of the prosthesis enters the intervertebral space by piercing or passing through an opening in the annulus fibrosus. As explained above, according to some embodiments the connector part 402 of the prosthesis 400 includes a leaf spring assembly 413 that facilitates its attachment to the anchor 200.

To deploy the active part 406 of the prosthesis 400 in the intervertebral space the rotatable grip 303a is rotated in the first direction to cause the pusher 306 at the end of tube 305b to apply a distally directed force on the active part 406 to force the active part out of the sleeve 401 while simultaneously retracting the tube 305a in the direction of the handle 310 to move the sleeve 401 proximally away from the repair site.

Figure 9B:
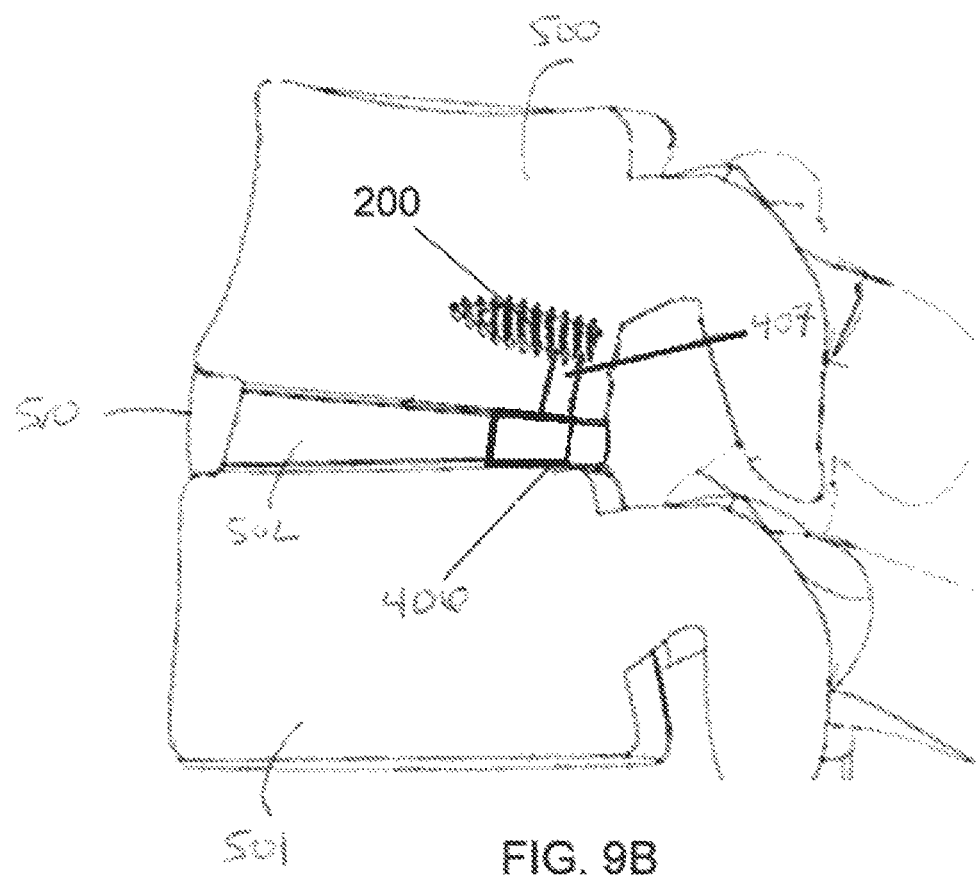

FIG. 9B shows the prosthesis placement tool 300 removed, leaving the prosthesis 400 arranged and secured to the vertebra 500 with the active part 406 being deployed inside the nucleus 502 of the intervertebral disc.

As noted above, when use of the prosthesis placement tool 300 is complete, tubes 305b and 305c are removed from the handle 310 as shown in FIG. 10A. This enables the parts of the tool 300 to be washed and disinfected after each use.

As discussed above, according to some embodiments the anchor 200 is provided with an elongate wire 210 and the connector part 402 of the prosthesis 400 is provided with a through hole 410 adapted for being traversed by the wire. In such a case, tube 305c may be provided with a passage adapted for receiving a proximal end the wire to assist in guiding the connector part 402 of the prosthesis in the direction of the anchor 200.

As will be discussed in more detail below, guide wire 210 of the anchor 200 can further be an electrical conductor and used in determining whether or not the connector part 402 of the prosthesis 400 is properly coupled to the anchor 200. In such an instance, the prosthesis placement tool 300 may further comprise an electrical warning circuit provided with two terminals adapted for generating a warning signal when the two terminals are electrically connected, one of the terminals being adapted for being connected to the guide wire 210 and the other terminal being connected to the end of the push means 302.

Figure 11:
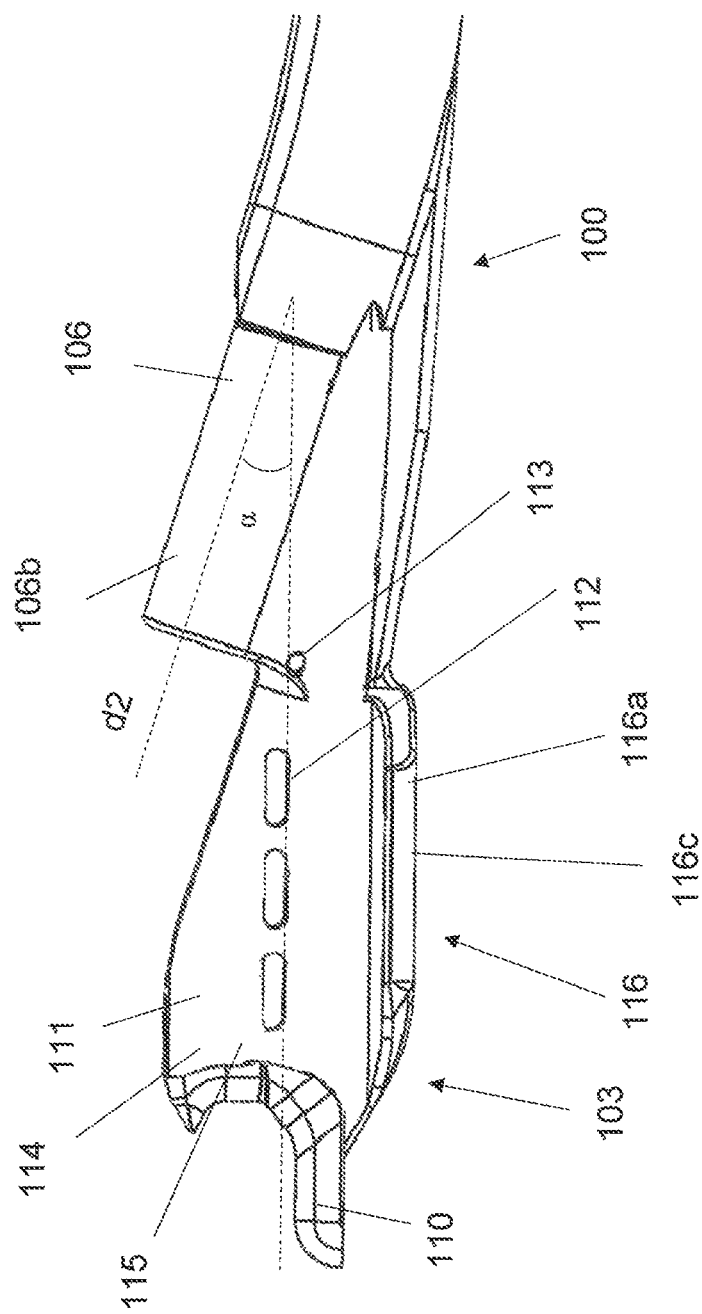
FIG. 11 illustrates a side view of the distal end portion of an anchor placement tool according to another embodiment.
Figure 12:
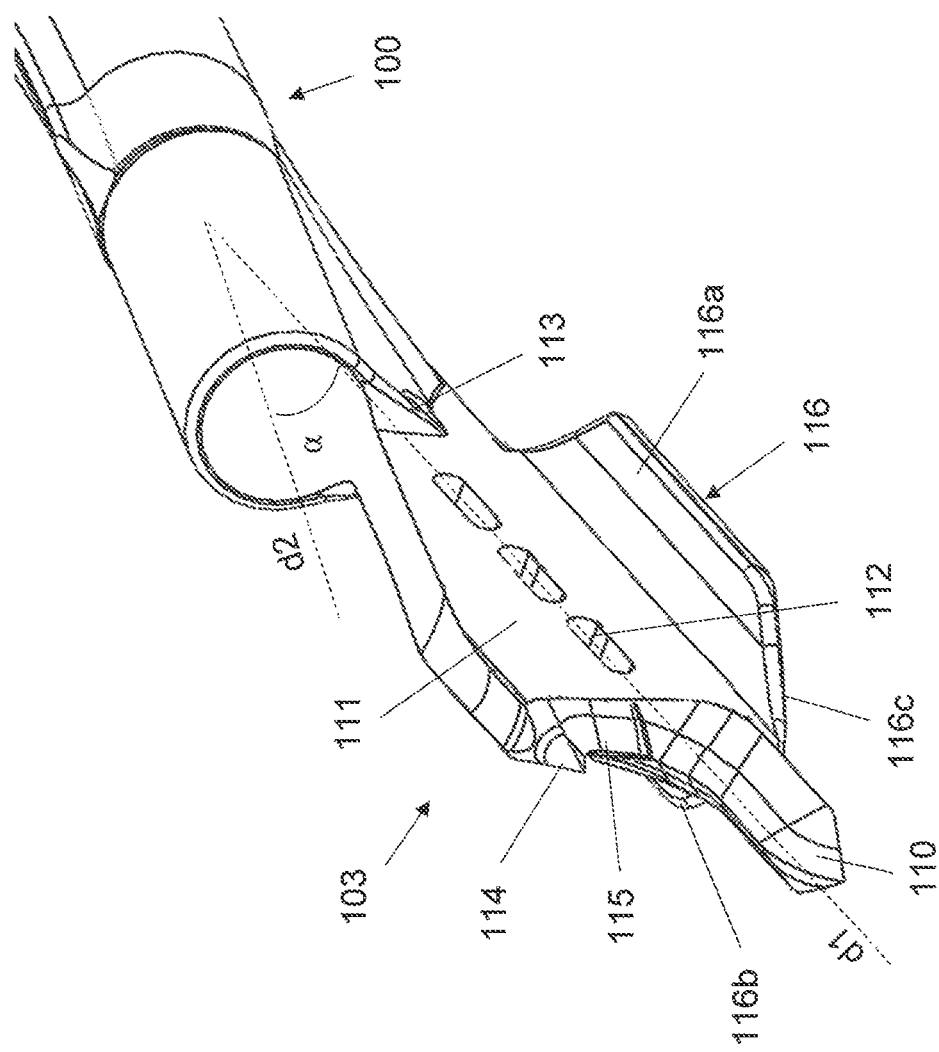
FIG. 12 illustrates a perspective view of the distal end portion of the anchor placement tool of FIG. 11.
Figure 13B:
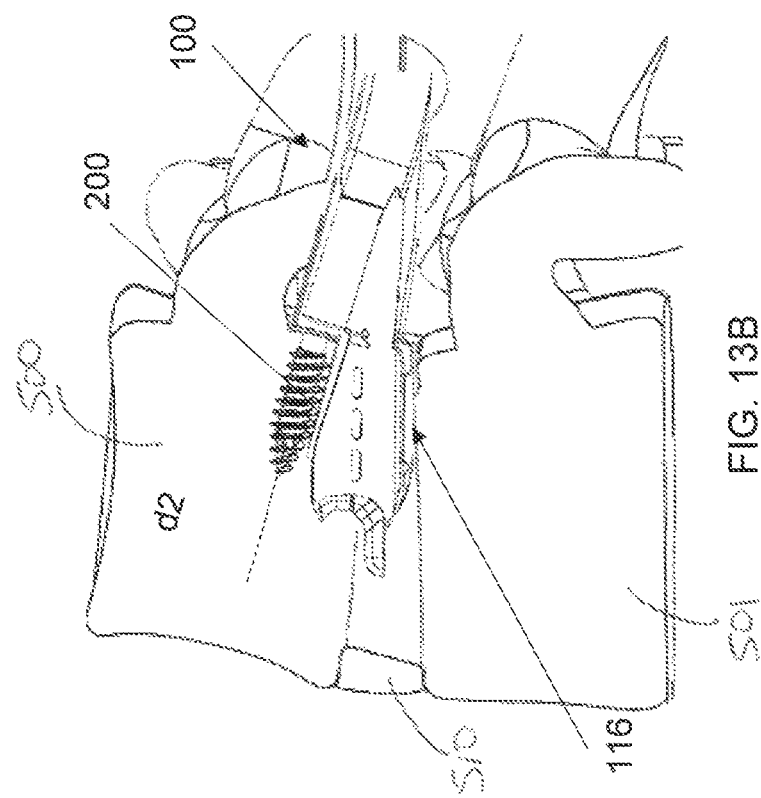
FIGS. 13A and 13B show a sequence of implanting an anchor in a vertebra by means of the anchor placement tool of FIGS. 11 and 12.
Figure 13A:
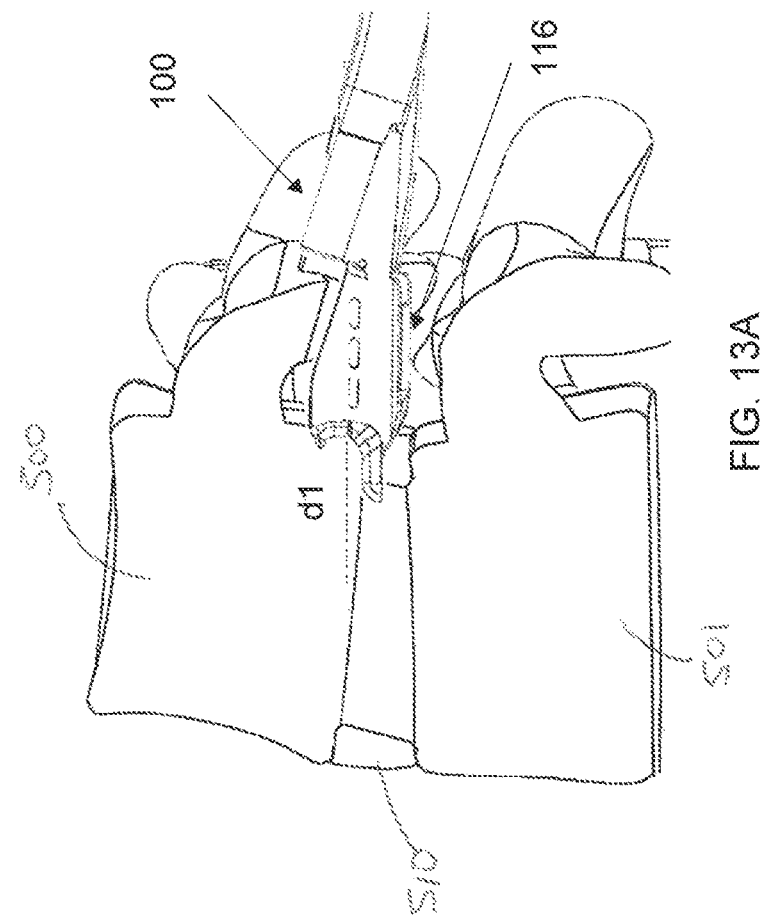

As shown in FIGS. 13A and 13B, the intervertebral disc 510 is located between vertebra 500 and vertebra 501, with the anchor 200 being secured to vertebra 500. FIGS. 11 and 12 illustrate a distal end portion of an anchor placement tool 100 according to another embodiment, the remainder of the tool 100 being as described above. In the embodiment of FIGS. 11 and 12, the chisel comprises support means 116 to further facilitate the placing and carving of the chisel. The support means 116 in the illustrated example includes two fins 116a and 116b that extend in opposite directions in a direction that may be perpendicular to the carving direction d1. The support means 116 provides a lower support surface 116c that allows the chisel to be supported on vertebra 501 during the carving and screwing operation of the anchor 200 as shown in FIGS. 13A and 13B. According to one embodiment, at least a portion of the cutting edge 115 is located in a plane perpendicular to the lower support surface 116c. The thickness of the support means 116 is suitably sized such that it occupies at least a part of the intervertebral space, such that as the lower support surface 116c rests on vertebra 501, the cutting mouth 103 is correctly arranged on vertebra 500.

After the anchor 200 has been secured to vertebra 500 and the connector part 402 of the prosthesis 400 has coupled to the anchor, it is important to confirm that the connector part 402 is properly secured inside the housing of the anchor. As discussed above, checking means may be employed to determine proper placement of the connector part 402 of the prosthesis 400 inside the housing of the anchor 200. According to one embodiment, the checking means is integrated in and forms a part of the prosthesis placement tool 300. As will be discussed in more detail below, according to other embodiments the checking means comprises a tool separate from the prosthesis placement tool 300.

FIGS. 19A through 20B illustrate an embodiment wherein the checking means is integrated in and forms a part of the prosthesis placement tool 300. According to one embodiment, the checking means includes a battery 501 comprising a first pole 501a and a second pole 501b. Electrically coupled to the first pole 501a is an electronic acoustic device 502 and tube 305c. According to some embodiments, the battery and electronic acoustic device are a part of an electronic cap 500 that is removably coupled to an end of the rotatable grip 303b. Tube 305c is made of an electrically conductive material and has a distal end 302 that is configured to make contact with the electrically conductive body of the anchor 200 only when the connector part 402 of the prosthesis has been properly secured to the anchor. When the connector part 402 of the prosthesis has not been properly secured to the anchor, the end 302 of tube 305c is not capable of making contact with the anchor.

Figure 19A:
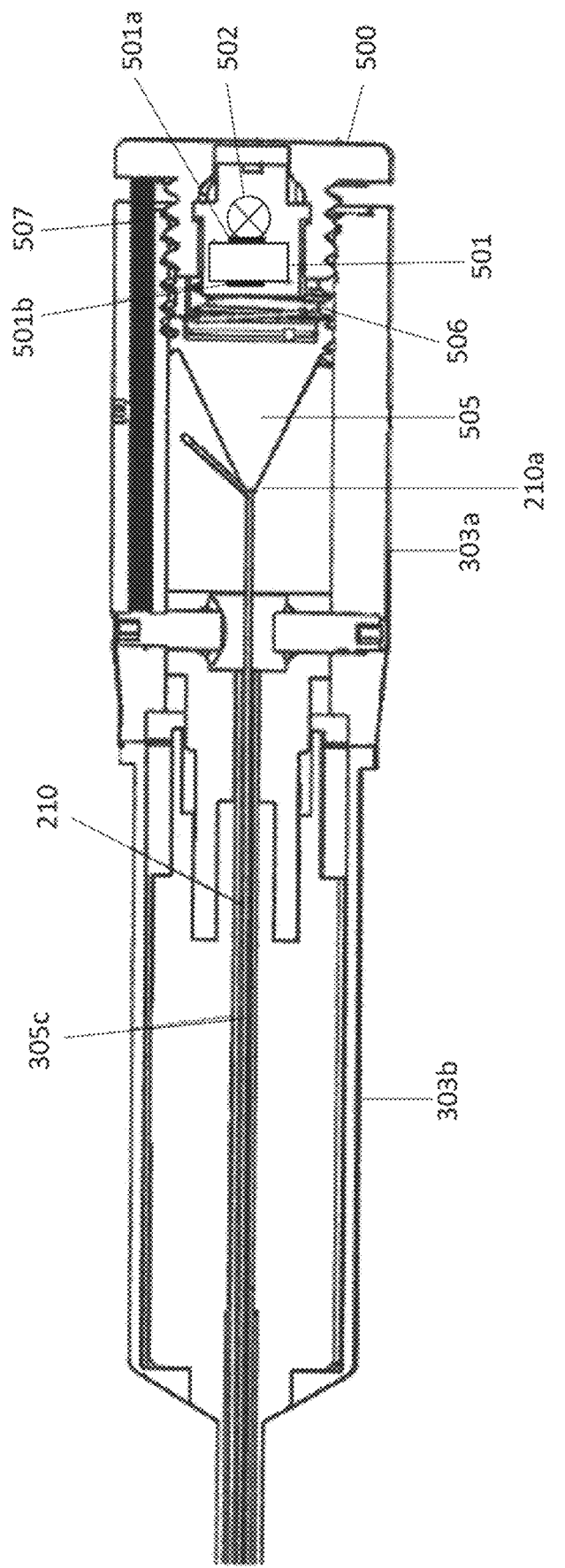
FIGS. 19A-B illustrate an embodiment of the prosthesis placement tool having integrated therein checking means that is configured to determine a proper placement of the prosthesis connector inside the housing of the anchor.
Figure 19B:
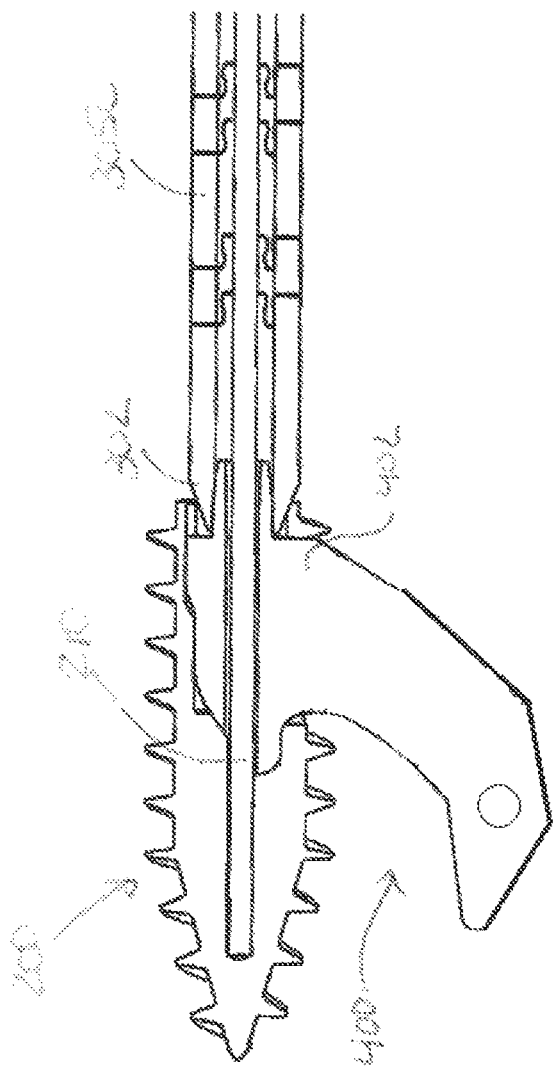
Figure 20A:
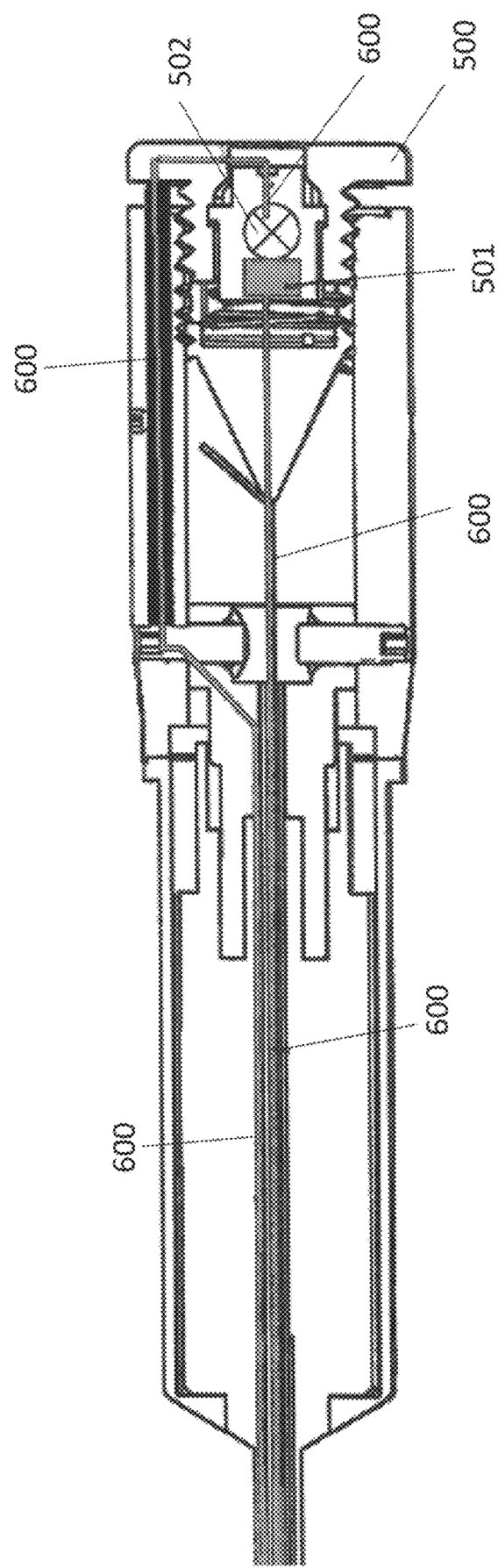
FIGS. 20A-B shows a current flow path through the electrical circuit of FIGS. 19A-B.

The anchor 200 includes the electrically conductive elongate wire 210 that has a first end portion-coupled to an interior of the anchor. The elongate wire 210 extends proximally from the anchor and is passed through the inner conduit of tube 305c during the checking process. According to one embodiment, the elongate wire and the tube 305c are electrically isolated from one another in order to prevent a short circuit between the two. The length of the elongate wire 210 is sufficient to pass through the tube 305c so that a proximal end portion 210a of the wire 210 is directly or indirectly electrically coupled to the second pole 501b of the battery 501. As shown in FIGS. 19A and 20A, according to one embodiment the checking means includes an electrically conductive part 505 that is electrically coupled to the second pole 501b of the battery 501. In the embodiment shown in the figures, the electrically conductive part has a conical shape, but is in no way limited to such a shape. When the distal end 302 of tube 305c contacts a proximal end portion of the anchor 200 as shown in FIGS. 19B and 20B, and the proximal end portion 210a of the elongate wire 210 contacts the electrically conductive part 505 inside the rotatable grip 303a, the electrical circuit disposed between the poles of the battery 501 closes to cause current to flow to the electronic acoustic device 502 to cause it to emit an audible sound.

In the embodiment of FIGS. 19A-20B, the electrically conductive part 505 is coupled to the second pole 501b of the battery 501 through a series of parts that include one or more electrically conductive elements 506. According to one embodiment, the first pole 501a of the battery 501 is coupled to tube 305c through a series of electrically conductive elements disposed inside the handle 310 of the prosthesis placement tool 300. According to one embodiment the electrically conductive elements include a conductor 507 arranged in an internal conduit of the rotatable grip 303a. The anchor 200, the prosthesis connector 402 and the distal end 302 of the elongate tube 305c are configured such that the distal end of the elongate tube can only make contact with the anchor upon the connector being properly and fully inserted and locked inside the housing of the anchor.

Figure 20B:
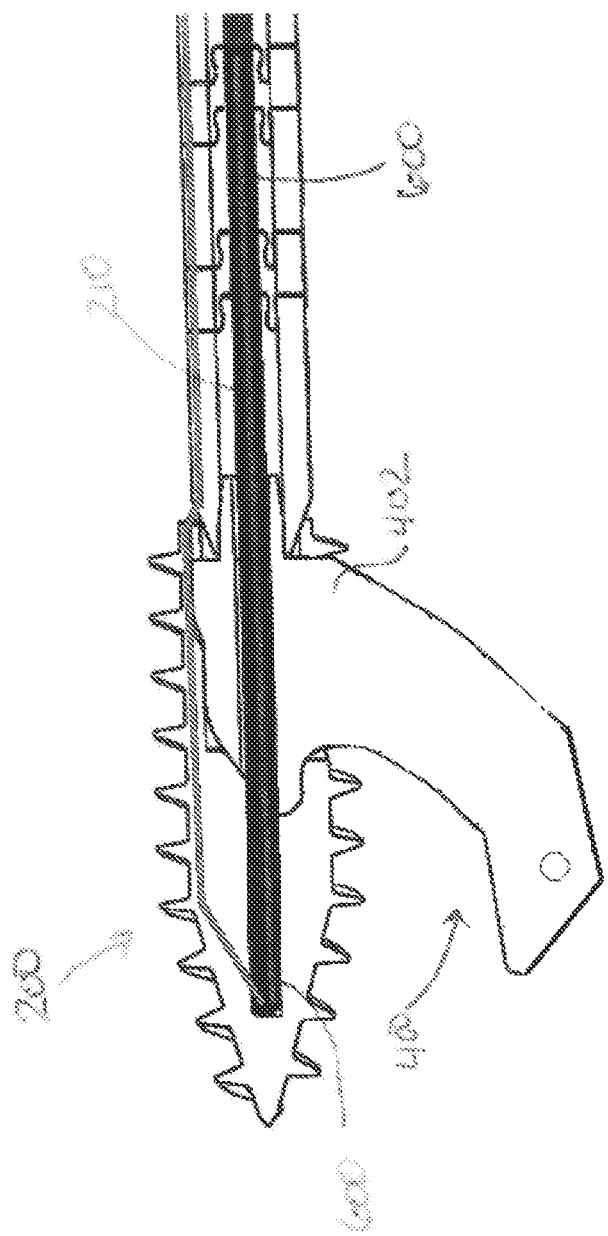

FIGS. 20A and 20B generally show an intended current flow path 600 when the checking means is in use. According to one embodiment, current flows from the first pole 501a of the battery 501 to the electronic acoustic device 502, then through an electrically conductive part (not shown) located in the cap 500. Current then flows through various electrically conductive parts inside the handle 310 and to a proximal portion of tube 305c. Current then flows distally along a length of the tube 305c and the pusher 302, and then into the body of the anchor 200. As a result of the anchor 200 and elongate wire 210 being electrically conductive, current continues to flow through the elongate wire and to the second pole 501b of the battery 501. In the embodiment of FIGS. 19A-20B current flows from the proximal end portion 210a of the elongate wire 210 to the enlarged electrically conductive part 505 and then through the one or more elements 506 electrically coupled to the second pole 501b of the battery.

Figure 21B:
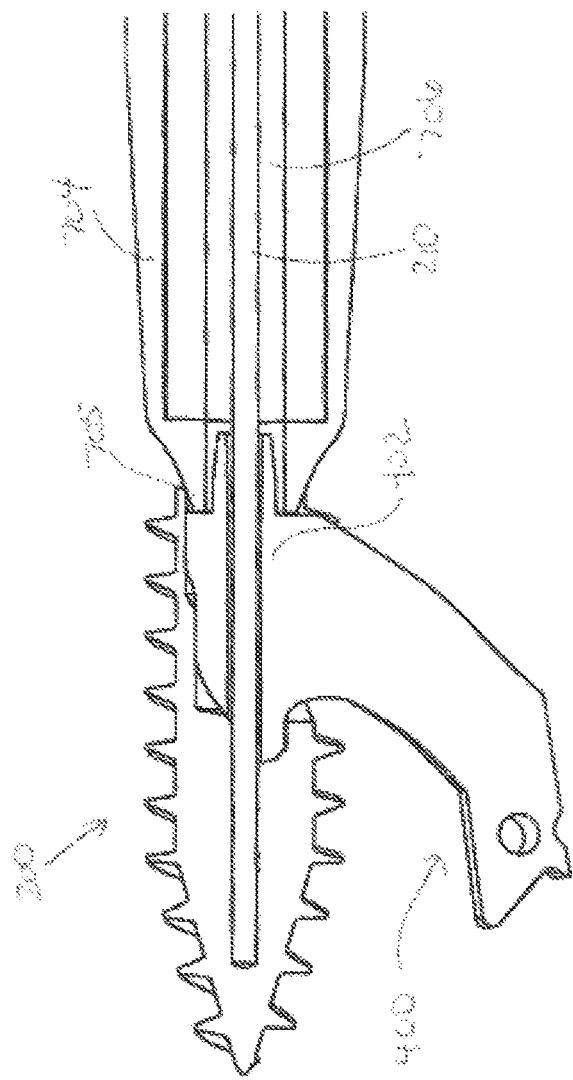
FIG. 21B shows a distal end portion of an electrically conductive elongate tube of the checker tool of FIG. 21A in contact with the anchor.
Figure 21C:
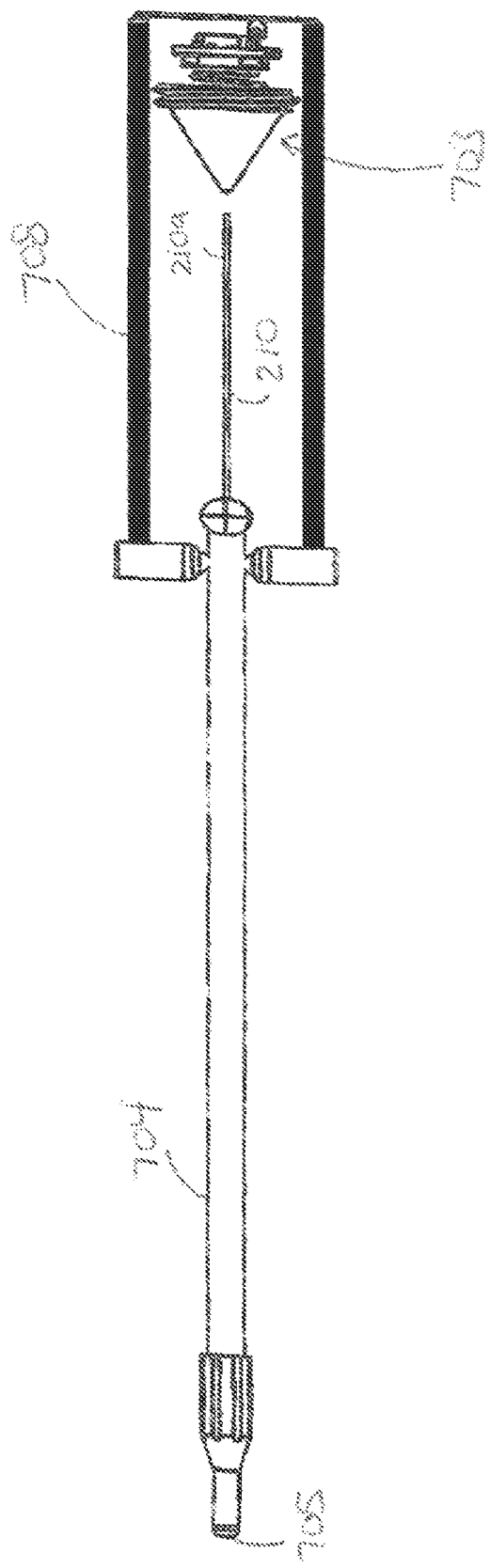
FIG. 21C generically shows electrical components inside the handle of the checker tool.

FIGS. 21A-C illustrate another embodiment wherein the checking means forms a part of an independent checker tool 700. The manner in which the checker tool functions is similar to that of that described above in reference to FIGS. 19A-20B.

As shown in FIG. 21A, the checker tool 700 includes a handle 702 that is configured to be gripped by a hand of a user. As shown in FIG. 21C, in one embodiment an electrical assembly 703 located inside the handle is the same or at least in part similar to the electrical assembly located inside the rotatable grip 303a of the prosthesis placement tool 300 shown in FIG. 19A. Extending distally from the handle 702 is an electrically conductive elongate tube 704 that has an end part 705 that is configured to make contact with at least a portion of the body of the anchor 200, as shown in FIG. 21B, when the connector part 402 of the prosthesis 400 is properly introduced and secured inside the housing of the anchor 200. As with the embodiment of FIGS. 19A-20B, the electrical assembly 703 includes a battery having first and second poles with an electronic acoustic device electrically coupled to the first pole. Also coupled to the first pole of the battery is the electrically conductive elongate tube 704. The elongate tube 704 includes an internal conduit 706 through which the electrically conductive elongate wire 210 of the anchor 200 passes when the distal end part 705 of the elongate tube 704 is in contact with the anchor. The length of the elongate wire 210 is sufficient to cause a proximal end segment 210a of the wire to contact the second pole of the battery directly or to contact a larger electrically conductive part (like 505 in FIG. 19A) that is electrically coupled to the second pole.

When the distal end part 705 of the elongate tube 704 makes contact with the body of the anchor 200 while the proximal end segment 210a of the elongate wire 210 is electrically coupled to the second pole of the battery, according to one embodiment current flows from the first pole 501a of the battery 501 to the electronic acoustic device 502, then through an electrically conductive part 708 located in the handle 702. Because the electrically conductive part 708 is electrically coupled to the elongate tube 704, current then flows distally through the electrically conductive elongate tube 704 and into the body of the anchor 200. As a result of the electrical circuit being closed, current flows through the electronic acoustic device causing it to sound to announce to the user of the device the prosthesis 400 is properly connected to the anchor 200.

Like the embodiment of FIGS. 19A-20B, the elongate wire 210 and the tube 704 are electrically isolated from one another in order to prevent a short circuit between the two.

According to one embodiment, a method of implanting an active part 406 of a prosthesis 400 into a nucleus of an intervertebral disc 510 is carried out by a surgeon through the use of the anchor placement tool 100 and the prosthesis placement tool 300 as contemplated and described above. Vertebra 500 is initially carved using the chisel of the anchor placement tool 100 as described above. The carving of the vertebra 500 is followed by screwing the anchor 200 into the vertebra. This is accomplished while the anchor is supported on the screwing means 109 and the rod 107 to which the screwing means is attached is rotated.

Upon the anchor being successfully positioned inside the vertebra 500 at a desired angular orientation, the prosthesis 400 is then coupled to the end of the prosthesis placement tool 300 with the sleeve 401 that houses the active part 406 of the prosthesis being attached to the distal end of tube 305a and the connector part 402 of the prosthesis being supported by the pusher 302 of tube 305c. The prosthesis placement tool 300 is then positioned such that at least a portion of the sleeve 401 is located inside the intervertebral disc 510 and such that the connector part 402 of the prosthesis 400 is aligned with the mouth 204 of the anchor 200. Tube 305c is then distally advanced to cause the pusher 302 to push the connector part 402 of the prosthesis into the housing of the anchor sufficient to cause the leaf springs 413a and 413b of the connector part to reside inside anchor recesses 208a and 208b. Thereafter, the active part 406 of the prosthesis 400 is advanced into the nucleus of the intervertebral disc 510 by a rotating of the rotatable grip 303a. As discussed above, rotating the grip 303a results in tube 305b being advanced distally so that the pusher 306 at its distal end pushes on the active part of the prosthesis to push it out of sleeve 401 and into the nucleus of the disc 510. The rotating of the grip 303a simultaneously causes a proximal retraction of tube 305a to cause the sleeve 401 to be moved proximally out of the intervertebral disc space.

In some instances, after the prosthesis 400 has been implanted, the checking means is subsequently used to determine whether or not the connector part 402 has been properly secured to the anchor 200. According to one embodiment this is achieved through the use a prosthesis placement tool having integrated therein the checking means as described above. According to another embodiment this is accomplished through the use of a checker tool distinct and separate from the prosthesis placement tool.

The following set of clauses A through E disclose in an unlimited way additional embodiments.

Clause Set A:

Clause 1. A tool for placing an anchor in a vertebra, the anchor including a threaded outer part, the tool comprising:
 a handle including a fixed handle portion and a rotatable handle portion;
 a chisel located at a distal end of the tool and joined to the fixed handle portion by an arm, the chisel configured to carve the vertebra in a carving direction when a force in a direction of the chisel is applied to the fixed handle portion, the arm including a conduit having an outlet that determines an outlet direction of the conduit, the outlet direction being different from the carving direction; and
 a rod coupled to and rotatable with the rotatable handle portion, the rod including a longitudinally flexible end portion and an end part that is configured to engage the anchor in a manner that results in a rotation of the anchor when the rotatable handle is rotated, the rod configured to be inserted into the conduit of the arm such that the end part protrudes from the outlet of the conduit.

Clause 2. The tool according to clause 1, wherein the chisel comprises a cutting mouth that includes a punch and a cutting fin, the punch being located distal to the cutting fin.

Clause 3. The tool according to clause 2, wherein the cutting fin includes a pointed projection located proximal to the punch.

Clause 4. The tool according to clause 3, wherein the cutting fin comprises a cutting edge that is disposed between the punch and the pointed projection.

Clause 5. The tool according to clause 4, wherein the cutting edge is curved.

Clause 6. The tool according to clause 1, wherein the chisel includes a plurality of markers that are longitudinally aligned in the carving direction.

Clause 7. The tool according to clause 6, wherein the plurality of markers includes a plurality of through holes that extend through a body of the chisel.

Clause 8. The tool according to clause 6, wherein the plurality of markers includes radiopaque markers disposed on a body of the chisel.

Clause 9. The tool according to clause 1, wherein the chisel includes a maximum carving marker.

Clause 10. The tool according to clause 9, wherein the maximum carving marker is a hole that extends through a body of the chisel.

Clause 11. The tool according to clause 9, wherein the maximum carving marker is radiopaque marker disposed on a body of the chisel.

Clause 12. The tool according to clause 6, wherein chisel includes a maximum carving marker that is located proximal to the plurality of markers Clause 13. The tool according to clause 1, wherein a distal end portion of the conduit of the arm includes a bend.

Clause 14. The tool according to clause 1, wherein the fixed handle portion includes a threaded shaft, and the rotatable handle portion includes a threaded part complementary to the threaded shaft, the threaded shaft of the fixed handle portion and the threaded part of the rotatable handle portion being operatively coupled to enable the rotatable handle portion to rotate with respect to the fixed handle portion.

Clause 15. The tool according to clause 1, wherein the handle includes a stop to limit rotation of the rotatable handle portion with respect to the fixed handle portion.

Clause 16. The tool according to clause 14, wherein the handle includes a stop to limit rotation of the rotatable handle portion with respect to the fixed handle portion, the stop being formed in at least one of the threaded shaft of the fixed handle portion and the threaded part of the rotatable handle portion.

Clause 17. The tool according to clause 1, wherein the chisel includes a lower support surface defined by first and second projections that extend in opposite directions and in a direction perpendicular to the carving direction.

Clause 18. The tool according to clause 1, wherein at least a distal end portion of the rod includes an internal conduit that is configured to house an elongate wire.

Clause Set B:

Clause 1. A method for placing an anchor in a first vertebra, the anchor including a threaded outer part, the method comprising:
  obtaining a tool that includes:
    a handle including a fixed handle portion and a rotatable handle portion;
    a chisel located at a distal end of the tool and joined to the fixed handle portion by an arm, the chisel configured to carve the first vertebra in a carving direction when a force in a direction of the chisel is applied to the fixed handle portion, the arm including a conduit having an outlet that determines an outlet direction of the conduit, the outlet direction being different from the carving direction; and
    a rod coupled to and rotatable with the rotatable handle portion, the rod including a longitudinally flexible end portion and an end part that is configured to engage the anchor in a manner that results in a rotation of the anchor when the rotatable handle is rotated, the rod configured to be inserted into the conduit of the arm such that the end part protrudes from the outlet of the conduit;
  supporting a proximal end portion of the anchor on the end part of the rod, the anchor being supported such that when the rod rotates the anchor also rotates;
  inserting the rod into the conduit of the arm so that the anchor does not protrude from the outlet of the conduit;
  applying one or more distally directed blunt forces to the handle to carve the first vertebra with the use of the chisel;
  advancing the rod distally in the conduit of the arm to cause the anchor to pass through the outlet of the conduit;
  pressing a distal tip of the anchor against the first vertebra by applying a distally directed force to the rotatable handle portion; and
  while applying the distally directed force to the rotatable handle portion, rotating the rotatable handle portion to cause the threaded outer part of the anchor to advance into the first vertebra.

Clause 2. The method according to clause 1, wherein the chisel includes a cutting mouth having a punch and a cutting fin, the punch being located distal to the cutting fin, the cutting fin including a pointed projection located proximal to the punch, the cutting fin including a cutting edge that is disposed between the punch and the pointed projection, the step of carving the first vertebra comprising:
  advancing the punch in the carving direction to cut a portion of a base of the first vertebra, the advancing of the punch being sufficient to cause the pointed projection to be embedded in the first vertebra before a carving of the first vertebra is carried out by the cutting edge.

Clause 3. The method according to clause 2, wherein the punch is advanced sufficiently to pierce an annulus fibrosis of an intervertebral disc located adjacent the first vertebra.

Clause 4. The method according to clause 2, wherein the cutting edge has a curved shape and is configured to produce a straight cut of the first vertebra between the punch and the pointed projection.

Clause 5. The method according to clause 1, wherein the chisel includes a plurality of markers that are longitudinally aligned in the carving direction, the method comprising aligning the markers with the carving direction prior to applying the one or more distally directed blunt forces to the fixed handle portion.

Clause 6. The method according to clause 5, wherein the plurality of markers include a plurality of through holes that extend through a metal body of the chisel, the method further comprising viewing the plurality of markers by x-ray to determine an orientation of the chisel.

Clause 7. The method according to clause 5, wherein the plurality of markers include radiopaque markers disposed on a body of the chisel, the method further comprising viewing the plurality of markers by x-ray to determine an orientation of the chisel.

Clause 8. The method according to clause 1, wherein the chisel includes a maximum carving marker in the form of a through hole extending through a body of the chisel, the method further comprising viewing the maximum carving marker by x-ray to ensure a maximum carving of the first vertebra is not exceeded.

Clause 9. The method according to clause 1, wherein the chisel includes a maximum carving marker in the form of a radiopaque marker located on a body of the chisel, the method further comprising viewing the maximum carving marker by x-ray to ensure a maximum carving of the first vertebra is not exceeded.

Clause 10. The method according to clause 1, wherein a distal end portion of the conduit of the arm includes a bend, the step of inserting the rod into the conduit of the arm until the anchor protrudes from the outlet of the conduit comprising passing the end part of the rod through the bend.

Clause 11. The method according to clause 1, wherein the fixed handle portion includes a threaded shaft, and the rotatable handle portion includes a threaded part complementary to the threaded shaft, the method further comprising operatively coupling the threaded shaft of the fixed handle portion and the threaded part of the rotatable handle portion to enable the rotatable handle portion to rotate with respect to the fixed handle portion.

Clause 12. The method according to clause 1, wherein the handle includes a stop to limit rotation of the rotatable handle portion with respect to the fixed handle portion, the step of rotating the handle to cause the threaded outer part of the anchor to bore into the first vertebra comprising rotating the rotatable handle portion until the stop limits the rotation.

Clause 13. The method according to clause 1, wherein the chisel includes a lower support surface, the method further comprising resting the lower support surface on a second vertebra while rotating the rotatable handle portion to cause the threaded outer part of the anchor to bore into the first vertebra.

Clause 14. The method according to clause 1, further comprising an elongate wire having a first end attached to an inner part of the anchor and a second end that protrudes from a proximal mouth of the anchor, a distal end portion of the rod comprising an internal conduit, the method of supporting the proximal end portion of the anchor on the end part of the rod further comprising inserting the second end of the elongate wire into the internal conduit of the rod.

Clause Set C:

Clause 1. A tool for coupling a prosthesis to an anchor secured to a vertebra and for placing an active portion of the prosthesis located in a sleeve into an intervertebral disc located adjacent the vertebra, the tool comprising:
 a handle including an inner housing and a rotatable grip;
 a rod attached to the handle, a distal end portion of the rod including a longitudinal flexible part, the rod including a distal end part configured to act on a connector of the prosthesis for the purpose of securing the connector to the anchor;
 a first tube operatively coupled to the rotatable grip such that upon the rotatable grip being rotated in a first direction, a distal end of the first tube linearly moves towards the handle, a distal end portion of the first tube including one or more securing elements that facilitate an attachment of the sleeve to the first tube; and
 a second tube operatively coupled to the rotatable grip such that upon the rotatable grip being rotated in the first direction, a distal end of the second tube linearly moves away from the handle, the distal end of the second tube including a pusher to push the active portion of the prosthesis out of the sleeve and into the intervertebral disc.

Clause 2. The tool according to clause 1, wherein at least a portion of the second tube is located inside the first tube.

Clause 3. The tool according to clause 2, wherein at least a portion of the rod is located inside the second tube.

Clause 4. The tool according to clause 1, wherein the first tube is operatively coupled to the rotatable grip by a first spindle nut assembly and the second tube is operatively coupled to the rotatable grip by a second spindle nut assembly.

Clause 5. The tool according to clause 4, wherein the first and second spindle nut assemblies are concentrically aligned.

Clause 6. The tool according to clause 4, wherein the first and second spindle nut assemblies reside inside the inner housing of the handle.

Clause 7. The tool according to clause 1, wherein the distal end part of the rod is a screwdriver.

Clause 8. The tool according to clause 1, wherein the one or more securing elements of the distal end portion of the first tube comprise one or more tabs configured for placement inside on or more openings in the sleeve.

Clause 9. The tool according to clause 1, further comprising an electronic cap configured to be coupled to the handle, the electronic cap including an electric circuit that includes an electronic acoustic device electrically coupled to a first pole of a battery, the rod being electrically conductive and electrically coupled to the first pole of the battery when the electronic cap is coupled to the handle.

Clause 10. The tool according to clause 9, wherein the electric circuit is configured such that the electronic acoustic device is energized upon the distal end part of the rod making contact with the anchor and an elongate wire attached to the anchor being electrically coupled to a second pole of the battery.

Clause 11. The tool according to clause 4, wherein the rod and the second tube are each separable from the handle.

Clause Set D:

Clause 1. A method for coupling a prosthesis to an anchor secured to a vertebra and for placing an active portion of the prosthesis located in a sleeve into an intervertebral disc located adjacent the vertebra, the prosthesis including a connector configured to connect the prosthesis to the anchor and an extension that couples the connector to the active portion, the method comprising:
 obtaining a tool that includes:
  a handle including an inner housing and a rotatable grip;
  a rod attached to the handle, a distal end portion of the rod including a longitudinal flexible part, the rod including a distal end part configured to act on the connector of the prosthesis for the purpose of securing the connector to the anchor;
  a first tube operatively coupled to the rotatable grip such that upon the rotatable grip being rotated in a first direction, a distal end of the first tube linearly moves towards the handle; and
  a second tube operatively coupled to the rotatable grip such that upon the rotatable grip being rotated in the first direction, a distal end of the second tube linearly moves away from the handle, the distal end of the second tube including a pusher for pushing the active portion of the prosthesis out of the sleeve and into the intervertebral disc;
 attaching the sleeve to a distal end portion of the first tube;
 positioning the prosthesis so that the connector is at least partially aligned with a proximal end of the anchor and the sleeve is partially disposed inside the intervertebral disc;
 rotating the rotatable grip in the first direction to cause the sleeve to be moved away from the intervertebral disc and towards the handle and to cause the pusher to move away from the handle to push the active portion of the prosthesis out of the sleeve and into the intervertebral disc.

Clause 2. The method according to clause 1, wherein the connector of the prosthesis comprises a projection that is configured to be inserted into a housing of the anchor, the projection including a leaf spring assembly having one or more leaf springs that are configured to interlock with one or more recesses of a wall that defines an inner housing of the anchor, the method further comprising:
- positioning the prosthesis so that the connector is at least partially aligned with a proximal end of the anchor; and
- pushing on the handle to cause the distal end part of the rod to push on the connector to force the one or more leaf springs into the housing of the anchor to cause the connector to be interlocked with the anchor.

Clause 3. The method according to clause 2, wherein an elongate wire is attached to the wall of the anchor and protrudes proximally from a proximal mouth of the housing, the projection of the connector of the prosthesis including an internal conduit, the rod also including an internal conduit, the step of positioning the prosthesis so that the connector is at least partially aligned with a proximal end of the anchor comprising inserting at least a portion of the elongate wire into the internal conduit of each of the projection and rod.

Clause 4. The method according to clause 1, wherein at least a portion of the second tube is located inside the first tube.

Clause 5. The method according to clause 4, wherein at least a portion of the rod is located inside the second tube.

Clause 6. The method according to clause 1, wherein the first tube is operatively coupled to the rotatable grip by a first spindle nut assembly and the second tube is operatively coupled to the rotatable grip by a second spindle nut assembly.

Clause 7. The method according to clause 6, wherein the first and second spindle nut assemblies are concentrically aligned.

Clause 8. The method according to clause 6, wherein the first and second spindle nut assemblies reside inside the inner housing of the handle.

Clause 9. The method according to clause 6, further comprising separating the rod and the second tube from the handle and subsequently disinfecting the rod and the second tube.

Clause 10. The method according to clause 2, wherein the anchor is electrically conductive and electrically coupled to an electrically conductive elongate wire that is attached to an inner wall of the anchor, the method further comprising determining the connector of the prosthesis is properly interlocked with the anchor, the method including:
- attaching an electronic cap to the handle, the electronic cap comprising an electric circuit that includes an electronic acoustic device electrically coupled to a first pole of a battery,
- electrically coupling the first pole of the battery to the rod;
- placing a proximal end portion of the elongate wire inside an internal conduit of the rod;
- distally advancing the handle to cause the distal end part of the rod to make contact with a surface of the anchor and to cause a proximal end of the elongate wire to be electrically coupled to the second pole of the battery, the electric circuit configured to cause an activation of the electronic acoustic device upon the distal end part of the rod making contact with the surface of the anchor and the proximal end of the elongate wire being electrically coupled to the second pole of the battery, the activation of the electronic acoustic device being indicative of the connector of the prosthesis being properly interlocked with the anchor.

Clause Set E:

Clause 1. A tool for determining a connector part of a prosthesis is properly positioned inside a housing of an anchor embedded in a vertebra, the anchor including a body made of an electrically conductive material, an elongate electrically conductive wire being coupled to the anchor and having a proximal end portion extending proximally outside the housing, the tool comprising:
- a handle;
- an electrically conductive hollow tube extending distally from the handle and having a distal end part that is configured to act on the connector to press the connector inside the housing of the anchor, the distal end part configured to contact the anchor only when the connector of the prosthesis is properly positioned inside the anchor, the electrically conductive hollow tube including an internal conduit configured to receive the proximal end portion of the elongate wire; and
- an electric circuit that includes an electronic acoustic device electrically coupled to a first pole of a battery, the electrically conductive hollow tube also being electrically coupled to the first pole of the battery, the electric circuit including an electrically conductive part electrically coupled to a second pole of the battery and configured to contact a proximal end segment of the elongate wire when the distal end part of the electrically conductive hollow tube contacts the anchor, the electric circuit being configured to cause the electronic acoustic device to activate when the distal end part of the electrically conductive hollow tube contacts the anchor and when the proximal end segment of the elongate wire contacts the electrically conductive part.

Clause 2. The tool according to clause 1, wherein the battery and electronic acoustic device are located inside the handle.

Clause 3. The tool according to clause 1, wherein the battery and electronic acoustic device are located on a removable cap fixed to a proximal end of the handle.

Clause 4. The tool according to clause 1, wherein the electrically conductive part of the electric circuit is coupled to the second pole of the battery by a spring element.

Clause 5. The tool according to clause 1, wherein the electric circuit includes a metal washer or disc that electrically couples the hollow tube to the first pole of the battery.

Clause 6. The tool according to clause 1, wherein the electrically conductive part is cone-shaped.

What is claimed is:

1. A tool for placing an anchor in a vertebra, the anchor including a threaded outer part, the tool comprising:
- a handle including a fixed handle portion and a rotatable handle portion;
- a chisel located at a distal end of the tool and joined to the fixed handle portion by an arm, the chisel configured to carve the vertebra in a carving direction when a force in a direction of the chisel is applied to the fixed handle portion, the arm including a conduit having an outlet that determines an outlet direction of the conduit, the outlet direction being different from the carving direction; and
- a rod coupled to and rotatable with the rotatable handle portion, the rod including a longitudinally flexible end portion and an end part that is configured to engage the anchor in a manner that results in a rotation of the anchor when the rotatable handle is rotated, the rod configured to be inserted into the conduit of the arm such that the end part protrudes from the outlet of the conduit.

2. The tool according to claim 1, wherein the chisel comprises a cutting mouth that includes a punch and a cutting fin, the punch being located distal to the cutting fin.

3. The tool according to claim 2, wherein the cutting fin includes a pointed projection located proximal to the punch.

4. The tool according to claim 3, wherein the cutting fin comprises a cutting edge that is disposed between the punch and the pointed projection.

5. The tool according to claim 4, wherein the cutting edge is curved.

6. The tool according to claim 1, wherein the chisel includes a plurality of markers that are longitudinally aligned in the carving direction.

7. The tool according to claim 6, wherein the plurality of markers includes a plurality of through holes that extend through a body of the chisel.

8. The tool according to claim 6, wherein the plurality of markers includes radiopaque markers disposed on a body of the chisel.

9. The tool according to claim 1, wherein the chisel includes a maximum carving marker.

10. The tool according to claim 9, wherein the maximum carving marker is a hole that extends through a body of the chisel.

11. The tool according to claim 9, wherein the maximum carving marker is radiopaque marker disposed on a body of the chisel.

12. The tool according to claim 6, wherein the chisel includes a maximum carving marker that is located proximal to the plurality of markers.

13. The tool according to claim 1, wherein a distal end portion of the conduit of the arm includes a bend.

14. The tool according to claim 1, wherein the fixed handle portion includes a threaded shaft, and the rotatable handle portion includes a threaded part complementary to the threaded shaft, the threaded shaft of the fixed handle portion and the threaded part of the rotatable handle portion being operatively coupled to enable the rotatable handle portion to rotate with respect to the fixed handle portion.

15. The tool according to claim 1, wherein the handle includes a stop to limit rotation of the rotatable handle portion with respect to the fixed handle portion.

16. The tool according to claim 14, wherein the handle includes a stop to limit rotation of the rotatable handle portion with respect to the fixed handle portion, the stop being formed in at least one of the threaded shaft of the fixed handle portion and the threaded part of the rotatable handle portion.

17. The tool according to claim 1, wherein the chisel includes a lower support surface defined by first and second projections that extend in opposite directions and in a direction perpendicular to the carving direction.

18. The tool according to claim 1, wherein at least a distal end portion of the rod includes an internal conduit that is configured to house an elongate wire.

* * * * *